United States Patent
Takahashi et al.

(10) Patent No.: US 7,535,226 B2
(45) Date of Patent: May 19, 2009

(54) NUCLEAR MAGNETIC RESONANCE IMAGING APPARATUS

(75) Inventors: Tetsuhiko Takahashi, Tokyo (JP); Tomohiro Goto, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 33 days.

(21) Appl. No.: 11/666,599

(22) PCT Filed: Oct. 27, 2005

(86) PCT No.: PCT/JP2005/019777

§ 371 (c)(1),
(2), (4) Date: Apr. 26, 2007

(87) PCT Pub. No.: WO2006/046639

PCT Pub. Date: May 4, 2006

(65) Prior Publication Data

US 2008/0111546 A1    May 15, 2008

(30) Foreign Application Priority Data

Oct. 29, 2004   (JP)   .............................. 2004-315882

(51) Int. Cl.
*G01V 3/00* (2006.01)
(52) U.S. Cl. ...................................... 324/309; 324/307
(58) Field of Classification Search ................. 324/309, 324/307, 306
See application file for complete search history.

(56) References Cited

U.S. PATENT DOCUMENTS

| | | | |
|---|---|---|---|
| 6,479,996 B1 | 11/2002 | Hoogeveen et al. | |
| 6,584,337 B2 * | 6/2003 | Dumoulin et al. | 600/410 |
| 6,801,034 B2 * | 10/2004 | Brittain et al. | 324/309 |
| 6,870,367 B2 * | 3/2005 | Kirsch | 324/309 |
| 2002/0115929 A1 | 8/2002 | Machida | |

FOREIGN PATENT DOCUMENTS

| | | |
|---|---|---|
| JP | 3-4837 | 1/1991 |
| JP | 6-311977 | 11/1994 |
| JP | 8-71056 | 3/1996 |
| JP | 2002-95646 | 4/2002 |
| JP | 2004-503270 | 2/2004 |

\* cited by examiner

*Primary Examiner*—Louis M Arana
(74) *Attorney, Agent, or Firm*—Cooper & Dunham, LLP

(57) ABSTRACT

There is provided an MRI apparatus that is capable of imaging ON/OFF in response to a biological gating signal and changing conditions for imaging, even while the moving bed imaging is performed, and further reducing a load on a subject to be examined, which is caused by fluctuations in the bed moving velocity. A controller that controls a bed to transport the examined subject in a static magnetic field and a unit to apply an RF magnetic field and a gradient magnetic field for imaging configures settings so that the bed moving velocity is kept constant considering an entire imaging time, and further controls the magnetic applying unit for applying the RF magnetic field and the gradient magnetic field so that a moving velocity of the FOV (imaging area) in the subject coordinate system is made different from the bed moving velocity.

29 Claims, 14 Drawing Sheets

NUCLEAR MAGNETIC RESONANCE IMAGING APPARATUS

TECHNICAL FIELD

This disclosure relates to a nuclear magnetic resonance imaging apparatus (hereinafter, referred to as "MRI apparatus") that measures an NMR signal emitted from hydrogen, phosphor, and the like within a subject to be examined and visualizes a nuclear density distribution, a relaxation time distribution, and the like. In particular, it relates to a method to suppress an artifact caused by a living body in the MRI apparatus employing an imaging method, referred to as "moving bed imaging method". This moving bed imaging method acquires an image of a portion being wide in a body axis direction, by acquiring the NMR data while continuously moving a table on which the examined subject is laid.

BACKGROUND

As one of methods to observe the systemic hemodynamics or metabolism by using the MRI apparatus, there is proposed a method (moving bed imaging method) that acquires an image while moving a table continuously (see Patent document 1).

With regard to the above moving bed imaging, there are also proposed several means such as using a signal processing to recover image degradation that occurs because the imaging is performed while moving the bed, and limiting a velocity at which the bed is moved to a low speed so that the image degradation may not occur.

The patent document 1 further proposes that in a full-body imaging by MRA (magnetic resonance angiography), a bed moving velocity is made higher for a body trunk whereas it is made slower for lower extremities, so as to perform the imaging with consideration for the imaging area to coincide with a region where a contrast agent is flowing through blood vessels.

Patent document 1: U.S. Pat. No. 6,912,415

Since a living body has a cardiac beat and respiratory movement, those may degrade an image quality when an image of the heart or the liver is acquired. In order to avoid this image degradation due to such movements of the living body, cardiac triggering, pulse triggering, and respiratory gating are widely employed. In addition, as a method to eliminate a body motion artifact that occurs due to the movement of the examined subject while one piece of MR image is generated, there is proposed a method in which a respiratory motion is monitored by using an external breath sensor or a navigator echo, for instance, and measurement is performed only when a position of the examined subject undergoes a predetermined displacement.

Also in the moving bed imaging method as described above, a technique to suppress the body motion is essential to obtain a favorable image. However, if a biological gating signal is applied to the moving bed imaging method, following disadvantages may occur.

That is, according to the biological gating method, an image is not acquired while a gating signal is OFF. However, even while the gating signal is OFF, the bed continues moving. Therefore, positions of the bed are discontinuous in measured data, resulting in that artifact is generated on the image. According to the technical concept to vary the bed moving velocity as disclosed by the patent document 1, the movement of the bed is turned ON and OFF in response to the biological gating signal, in order to avoid the occurrence of such artifact. In this particular case, after gating off, the movement is restarted from the position which is the same as the position before gating off, whereby the imaging positions can be rendered continuous in a series of data acquisition.

However, generally, when the movement of bed is stopped and restarted, a predetermined length of time is needed until the bed movement reaches a constant speed. Therefore, controlling of the speed becomes difficult and this is not practical. In addition, such intermittent driving of the bed may increase a load on the examined subject. Similar problems may occur also in the case where the bed moving velocity is controlled, considering the blood travel time that is different by location, as described in the patent document 1.

An aspect of this disclosure is to provide an approach to reduce a load on the examined subject due to a change of moving velocity of the transport unit, and further provide an image that is effective for diagnosis, responding to variations in conditions while imaging a wide area, in the MRI apparatus employing the moving bed imaging method.

In the conventional art, along with a movement of a bed as a transport unit for a test object, a field of view (FOV) (signal acquisition area) on the examined subject moves in a direction opposite to the direction of the bed movement, both moving at the same velocity. On the other hand, the above-mentioned aspect of this disclosure can involve, for example, controlling the FOV (signal acquisition area) to move at a speed different from the bed movement.

In an exemplary embodiment of this disclosure, a nuclear magnetic resonance imaging method is provided that acquires an image of an imaging region of the examined subject, in a static magnetic field space of a nuclear magnetic resonance imaging apparatus provided with an FOV being desirable, the imaging region being wider than the FOV, while moving the transport unit having the examined subject thereon including, a step (1) that moves the examined subject so that the imaging region of the examined subject passes through the space for imaging, a step (2) that relatively displaces the FOV with respect to the static magnetic field space, in response to information obtained from the examined subject during at least a part of a period when the examined subject is being moved, a step (3) that executes an imaging pulse sequence while the examined subject is being moved, and collects NMR signals from the examined subject, and a step (4) that reconstructs an image of the wide imaging region of the examined subject, by using the NMR signals.

It is to be noted here that the information obtained from the examined subject may be biological information directly acquired from the examined subject such as an electrocardiograph and sphygmograph, for example, further including all the other information that can be obtained regarding the examined subject, such as positional information according to body motion and shifting of the examined subject, and information obtained from the nuclear magnetic resonance signal.

In the nuclear magnetic resonance imaging method according to the present invention, in the step (2) that relatively displaces the FOV, the information obtained from the examined subject is biological information detected from the examined subject, and a moving velocity of the FOV for the examined subject is controlled to be different from each other between in a first period and in a second period while acquiring an image of the imaging region, in response to this biological information.

In the nuclear magnetic resonance imaging method according to the present invention, in the step (2) that relatively displaces the FOV, a direction of the relative displacement is controlled to be different from each other between in the first period and in the second period.

The nuclear magnetic resonance imaging method according to the present invention includes a step (5) that configures settings for a first area and a second area within the imaging region, prior to the step (3) that collects the NMR signals, further includes in the step (2) that relatively displaces the FOV, a step (6) that acquires positional information of the FOV for the examined subject, the information obtained from the examined subject is information indicating reaching that the FOV has reached each of the areas, and a moving velocity of the FOV for the examined subject is controlled to be different from each other between in the first area and in the second area, in response to the information indicating the reaching.

In the nuclear magnetic resonance imaging method according to the present invention, in the step (2) that relatively displaces the FOV, the direction of the relative displacement is controlled to be different from each other in the first area and in the second area.

In the nuclear magnetic resonance imaging method according to the present invention, in the step (3) that collects the NMR signals, imaging of at least a part of the imaging region, for instance, includes a synchronous imaging by using the biological information, the imaging is executed in the first period in response to the biological information, the imaging is suspended in the second period in response to the biological information, the direction of the relative displacement is opposite to the moving direction of the examined subject in the first period, and the direction of the relative displacement is the same as the moving direction of the examined subject in the second period.

In the nuclear magnetic resonance imaging method according to the present invention, in the step (3) that collects the NMR signals, the biological information is acquired from a biological signal, for example, obtained from at least one of the electrocardiograph, the sphygmograph, and a body motion monitor, in the step (1) that moves the examined subject, a moving velocity of the transport unit is determined by a total imaging time including the first period and the second period and a distance the transport unit has traveled for acquiring an image of the imaging region, in the step (2) that relatively displaces the FOV, the moving velocity of the FOV for the examined subject within the first period is determined by the total imaging time when no synchronous imaging is performed, and a distance that the transport unit has traveled for acquiring the image of the imaging region, the imaging is executed from a position of the FOV at the point when the imaging is suspended, and in the second period, the moving velocity of the FOV for the examined subject is set to zero and the position of the FOV for the examined subject is not moved.

In the nuclear magnetic resonance imaging method according to the present invention, in the step (3) that collects the nuclear magnetic resonance signal, imaging of the second area includes, for example, collecting of the NMR signals required for reconstructing a subject image, and collecting of the NMR signals required for detecting a body motion of the examined subject, and in the step (2), the moving velocity of the FOV for the examined subject is controlled to be lower in the second area than in the first area.

In the nuclear magnetic resonance imaging method according to the present invention, in the step (5) that configures settings of each of the areas, an imaging condition in the first area is set to be different from the imaging condition in the second area, for example, and in the step (2) that relatively displaces the FOV, the moving velocity of the FOV for the examined subject is controlled to be different from each other between in the first area and in the second area, in response to each of the imaging conditions.

In the nuclear magnetic resonance imaging method according to the present invention, in the step (5) that configures settings of each of the areas, for example, the imaging conditions are set such that the second area should have a spatial resolution higher than the first area, and in the step (2) that relatively displaces the FOV, the moving velocity of the FOV for the examined subject is controlled to be lower in the second area than in the first area.

In the nuclear magnetic resonance imaging method according to the present invention, in the step (5) that configures settings of each of the areas, for example, the imaging condition for the second area is set in such a manner that at least one of a slice number, a phase encoding number, and a slice encoding number is increased relative to the imaging condition for the first area.

In the nuclear magnetic resonance imaging method according to the present invention, in the step (5) that configures settings of each of the areas, the imaging conditions are set such that the second area should have a higher SN than the first area, and in the step (2) that relatively displaces the FOV, the moving velocity of the FOV for the examined subject is controlled to be lower in the second area than in the first area.

In the nuclear magnetic resonance imaging method according to the present invention, in the step (5) that configures settings of each of the areas, for example, the imaging conditions are set in such a manner that a number of averaging the nuclear magnetic resonance signals is increased in the imaging condition for the second area, relative to the imaging condition for the first area.

In the nuclear magnetic resonance imaging method according to the present invention, in the step (5) that configures settings of each of the areas, for example, the imaging conditions are set in such a manner that a size of the FOV in the first area and a size of the FOV in the second area are different from each other.

In the nuclear magnetic resonance imaging method according to the present invention, in the step (3) that collects the NMR signals includes an imaging using a contrast agent, and in the step (5) that configures settings of each of the areas, the first area and the second area are configured in such a manner that in the second area, the contrast agent moves at a velocity lower than the first area, and in the step (2) that relatively moves the FOV, the moving velocity of the FOV for the examined subject is controlled to be lower in the second area than in the first area.

The nuclear magnetic resonance imaging method includes a step (7) that obtains a mean flow velocity of the contrast agent within the imaging region, prior to the step (5) that configures settings of each of the areas, in the step (1) that moves the examined subject, the moving velocity of the transport unit is assumed as the mean flow velocity, and in the step (2) that relatively displaces the FOV, in order that the moving velocity of the FOV for the examined subject accords with the moving velocity of the contrast agent, a moving direction of the FOV for the examined subject is set to be opposite to the moving direction of the examined subject in the first area, and the moving direction of the FOV for the examined subject is made to be the same as the moving direction of the examined subject in the second area.

In the nuclear magnetic resonance imaging method according to the present invention, for example, in the step (5) that configures settings of each of the areas, the first area and the second area are configured in such a manner that the second area is set in an area where a body axis direction of the examined subject and the moving direction of the examined subject form a larger angle than in the first area, and in the step (2) that relatively displaces the FOV, the moving velocity of the FOV for the examined subject in the moving direction of the examined subject is controlled to be lower in the second area than in the first area.

In the nuclear magnetic resonance imaging method, in the step (2) that relatively displaces the FOV, for example, the FOV is moved along the body axis direction, and the moving velocity of the FOV in the body axis direction is made approximately identical between the first area and the second area.

In the nuclear magnetic resonance imaging method according to the present invention, for example, in the step (3) that collects the nuclear magnetic resonance signal from the examined subject, a high-frequency magnetic field is applied for exciting the FOV, and in the step (2) that relatively moves the FOV, a frequency of the high-frequency magnetic field is controlled so as to control the relative displacement of the FOV.

In the nuclear magnetic resonance imaging method according to the present invention, in the step (1) that moves the examined subject, for example, the moving velocity of the examined subject is kept constant during a period for acquiring an image of the imaging region.

In the nuclear magnetic resonance imaging method according to the present invention, in the step (1) that moves the examined subject, for example, the moving velocity of the examined subject is controlled to be different from each other between in the first period and in the second period.

In the nuclear magnetic resonance imaging method according to the present invention, in the step (4) that reconstructs the image, for example, an image of a part of the imaging region is reconstructed based on the NMR signals that have been obtained so far within at least a part of the period for acquiring an image of the imaging region.

The nuclear magnetic resonance imaging apparatus according to the present invention includes, a transport unit that transports a subject to be examined within a static magnetic field space including a desired FOV, an information obtaining unit that obtains information from the examined subject, a magnetic field application unit that applies a high-frequency magnetic field and a gradient magnetic field to the examined subject, a control means that controls the transport unit and the magnetic field application unit, and a signal processing unit that receives NMR signals generated from the examined subject to construct an image, wherein, in the nuclear magnetic resonance imaging apparatus that acquires the NRM signals while the examined subject is moved by the transport unit, and acquires an image of an imaging region wider than the FOV, the control unit controls the magnetic field application unit in such a manner that the FOV is relatively displaced with respect to the static magnetic field space, in response to the information from the examined subject, during at least a part of the period when the examined subject is moving.

In the nuclear magnetic resonance imaging apparatus according to the present invention, for example, the information obtaining unit that obtains information from the examined subject, obtains biological information from the examined subject, and the control unit controls the magnetic field application unit, in response to the biological information, in such a manner that the moving velocity of the FOV for the examined subject is made different from each other between in a first period and in a second period, while an image of the imaging region is acquired.

In the nuclear magnetic resonance imaging apparatus according to the present invention, for example, the information obtaining unit that obtains information from the examined subject, further obtains positional information of the FOV for the examined subject, and finds information indicating reaching that the FOV has reached the first area and the second area within the imaging region configured in advance, and the control unit controls the magnetic field application unit, in response to the information indicating the reaching, in such a manner that the moving velocity of the FOV for the examined subject is made different from each other between in the first period and in the second period.

In the nuclear magnetic resonance imaging apparatus according to the present invention, for example, the information obtaining unit that obtains the biological information is at least one of an electrocardiograph, a sphygmograph, and a body motion monitor, and the control unit controls the magnetic field application unit in such a manner that the imaging is performed during the first period in response to the biological information, and the imaging is suspended during the second period in response to the biological information.

In the nuclear magnetic resonance imaging apparatus according to the present invention, for example, the unit that obtains the positional information of the FOV includes an encoder provided on the transport unit, and obtains the positional information of the FOV on the examined subject based on information from the encoder and a frequency of the high-frequency magnetic field.

According to the present invention. In an aspect of this disclosure, imaging is performed while the subject to be examined is moved, and the FOV is relatively displaced with respect to the static magnetic field space while the examined subject (i.e., transport unit) is moved. Therefore, a load on the examined subject is reduced, which is caused by fluctuations in the moving velocity of the transport unit, and further, variations in conditions while imaging a wide area are addressed, thereby providing an image effective for diagnosis. As a way of example, in case of a synchronous imaging, even when the imaging is turned ON/OFF according to a gating signal, it is possible to maintain continuity of an area from which a signal is acquired, and an image without artifact can be obtained. With regard to a part of the imaging area, various imaging is available such as obtaining an image of high spatial resolution and an image of multiple slices, according to a request from a user. In the imaging utilizing a contrast agent, it is possible to acquire an image following a moving velocity of the contrast agent.

In another aspect of this disclosure, a moving velocity of the transport unit can be configured with consideration given to a total imaging time. Therefore, even if suspension or restarting of imaging and/or fluctuations in the imaging time occur due to various imaging, an effect caused by heterogeneity of the magnetic field can be suppressed to a negligible degree, and a favorable image can be acquired.

DENOTATION OF REFERENCE NUMERALS

101 . . . SUBJECT TO BE EXAMINED, 102 . . . STATIC MAGNETIC FIELD MAGNET, 103 . . . GRADIENT MAGNETIC FIELD COIL, 104 . . . RF COIL, 105 . . . RF PROBE, 106 . . . SIGNAL DETECTOR, 107 . . . SIGNAL PROCESSOR, 111 . . . CONTROLLER, 112 . . . BED (TRANSPORT UNIT), 114 . . . BED CONTROLLER, 115 . . . MONITORING MACHINE

BEST MODE FOR CARRYING OUT THE INVENTION

Hereinafter, exemplary embodiments of the present invention will be explained with reference to the accompanying drawings.

Figure 1:
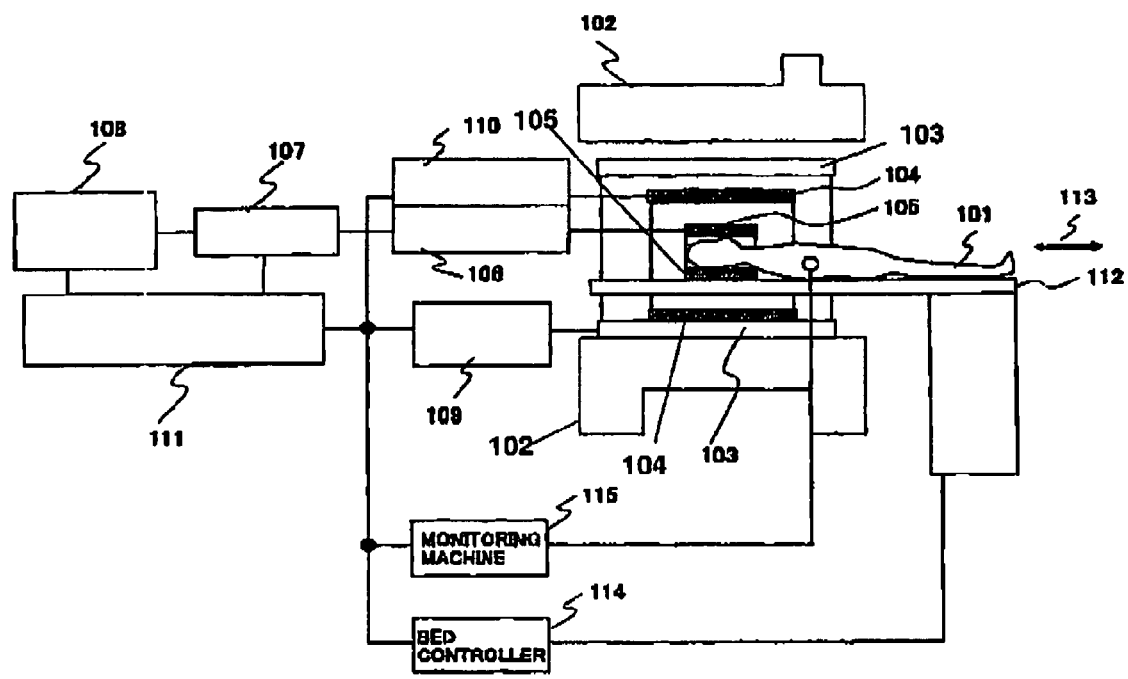
FIG. 1 illustrates an overview of an MRI apparatus in accordance with an exemplary embodiment of this disclosure.

FIG. 1 illustrates an overview of an MRI apparatus to which the present invention is applied.

This MRI apparatus is provided with a magnet 102 that generates a static magnetic field in a space into which a subject to be examined 101 is placed, a gradient magnetic field coil 103 that generates a gradient magnetic field within this space, an RF coil 104 that generates a high-frequency magnetic field in an imaging area of the examined subject, an RF probe 105 that detects nuclear magnetic resonance (MR) signals that are generated by the examined subject 101, and a bed 112 for introducing the examined subject 101 into to the static magnetic field space. A top panel of the bed 112 is provided with a detection unit, e.g., an encoder, so as to detect a position and a moved distance of the bed.

The gradient magnetic field coil 103 is made up of gradient magnetic field coils respectively in three directions (X, Y, Z) orthogonal to one another, and each generates a gradient magnetic field in response to a signal from a gradient magnetic field power source 109. According to a manner how these gradient magnetic fields are applied, an imaging section of the examined subject can be determined, and positional information is given to the MR signal.

Figure 2:
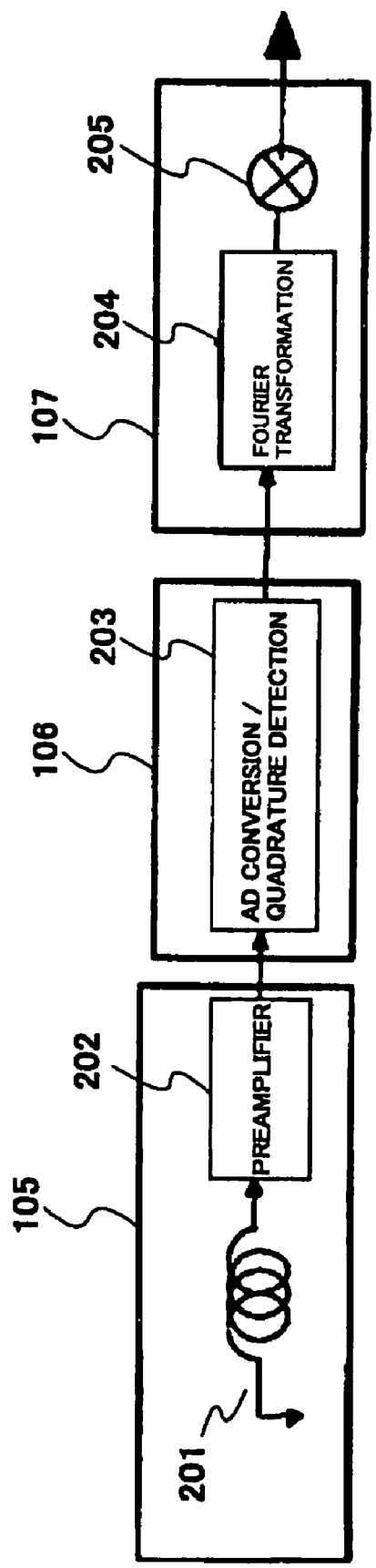
FIG. 2 illustrates details of a signal detector and a signal processor in the MRI apparatus of FIG. 1.

The RF coil 104 generates a high-frequency magnetic field in response to a signal from an RF transmitter 110. A signal from the RF probe 105 is detected by the signal detector 106 and the detected signal is subjected to a signal processing in the signal processor 107. Then, it is calculated to be converted into an image signal. FIG. 2 illustrates details of the signal detector 106 and the signal processor 107. As is shown, the signal detector 106 is made up of an AD conversion/quadrature detection circuit 203, and an NMR signal amplified by a preamplifier 202 of RF receiving coil 201 is subjected to quadrature detection by using a reference signal from a high-frequency generating circuit of the RF transmitter 110, as well as subjected to AD conversion be converted into two series of data, and then the converted data is passed to the signal processor 107. The signal processor 107 performs processing such as Fourier transformation, correction, and synthesis of data as appropriate, so as to reconstruct an image. The image is displayed on the display 108.

The gradient magnetic field power source 109, the RF transmitter 110, and the signal detector 106 are controlled by a controller 111. A control time chart is generally referred to as "pulse sequence", and various pulse sequences (imaging sequences), which are determined depending on a way how to perform imaging, are previously stored in a form of program, in a storage not illustrated. The controller 111 is provided with an input device (user interface: UI) for selecting an imaging sequence and for inputting an imaging parameter, and the like.

The bed 112 is movable in the direction indicated by an arrow 113 in the figure, and it is driven by a bed controller 114. The bed controller 114 follows a command from the controller 111 to move the bed 112 in a manner to be consistent with execution of an imaging sequence. A moving velocity of the bed, for example, a velocity to be moved in the direction from the head to feet, is 0.5 cm per second to 2.0 cm per second, typically.

In the present embodiment, the controller 111 inputs a signal from a monitoring machine 115 that monitors a biological signal from the examined subject 101, and controls execution of the imaging sequence based on the biological signal. The monitoring machine 115 monitors, for example, a beat, a pulse wave, an electrocardiographic waveform, and a respiratory motion, and the like, and the monitored data is converted into an electrical signal or an optical signal. Then, the converted data is transmitted to the controller 111 in real time.

Figure 3:
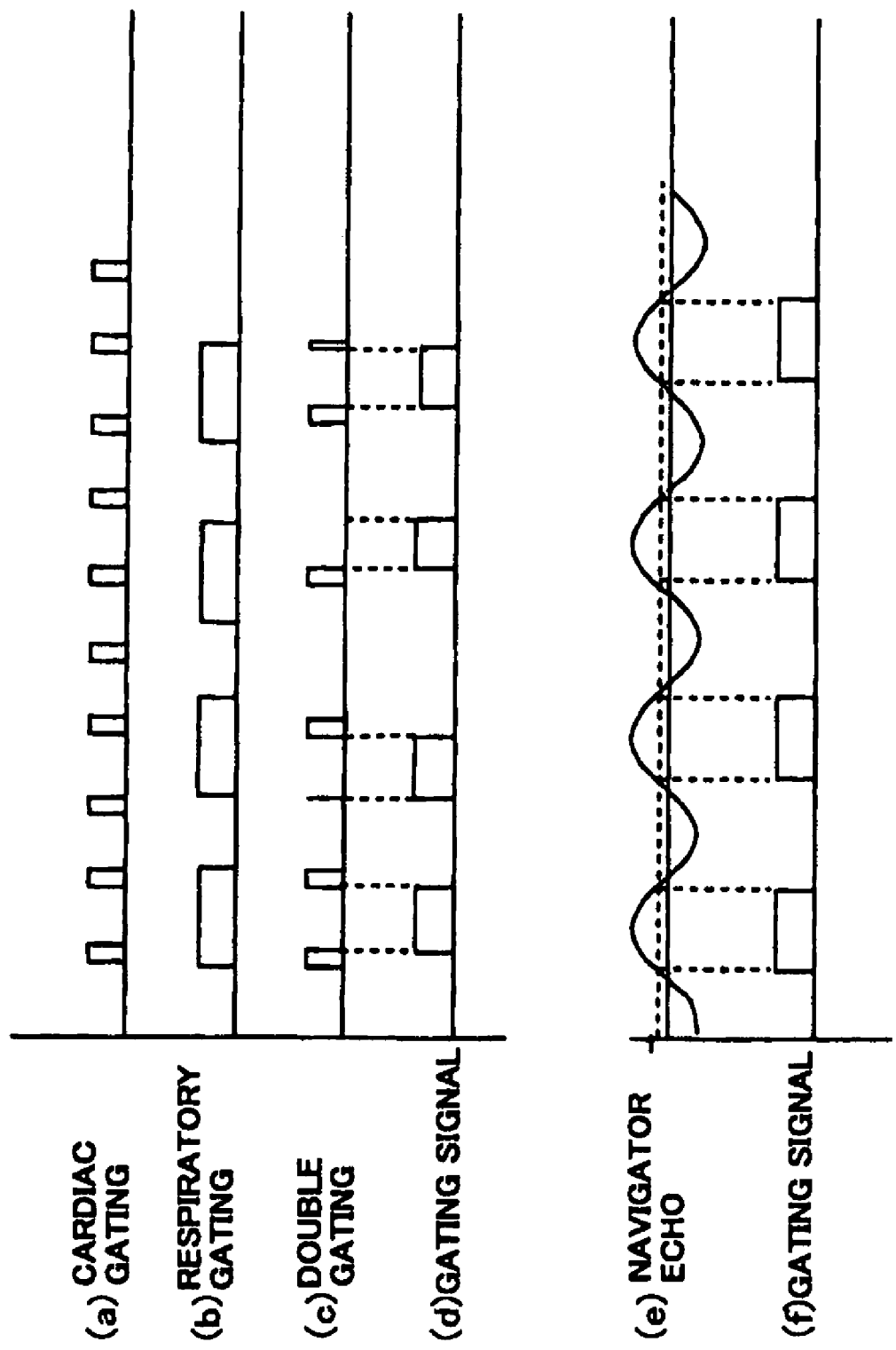
FIG. 3 is an illustration for explaining double gating.

As the monitoring machine 115, for example, there are provided an electrocardiograph and a respiratory motion sensor that detects abdominal vertical motions of the examined subject, and in imaging, cardiac gating or respiratory gating may be employed, or double gating combining the two gating may be employed. FIG. 3 shows an example of gating signal in the case where the double gating is employed. In the figure, (a) indicates a signal (R wave) from the electrocardiograph, (b) indicates a position signal from the respiratory motion sensor, (c) is AND signal of (a) and (b), and (d) indicates a gating signal. In the case of the double gating, the controller 111 controls imaging ON/OFF by using the gating signal. The gating signal turns the imaging ON when the signal from the electrocardiograph is placed between R-wave and R-wave and the position signal from the respiratory motion sensor is within a predetermined range of the examined subject. At all other cases, the imaging is turned OFF.

Figure 4:
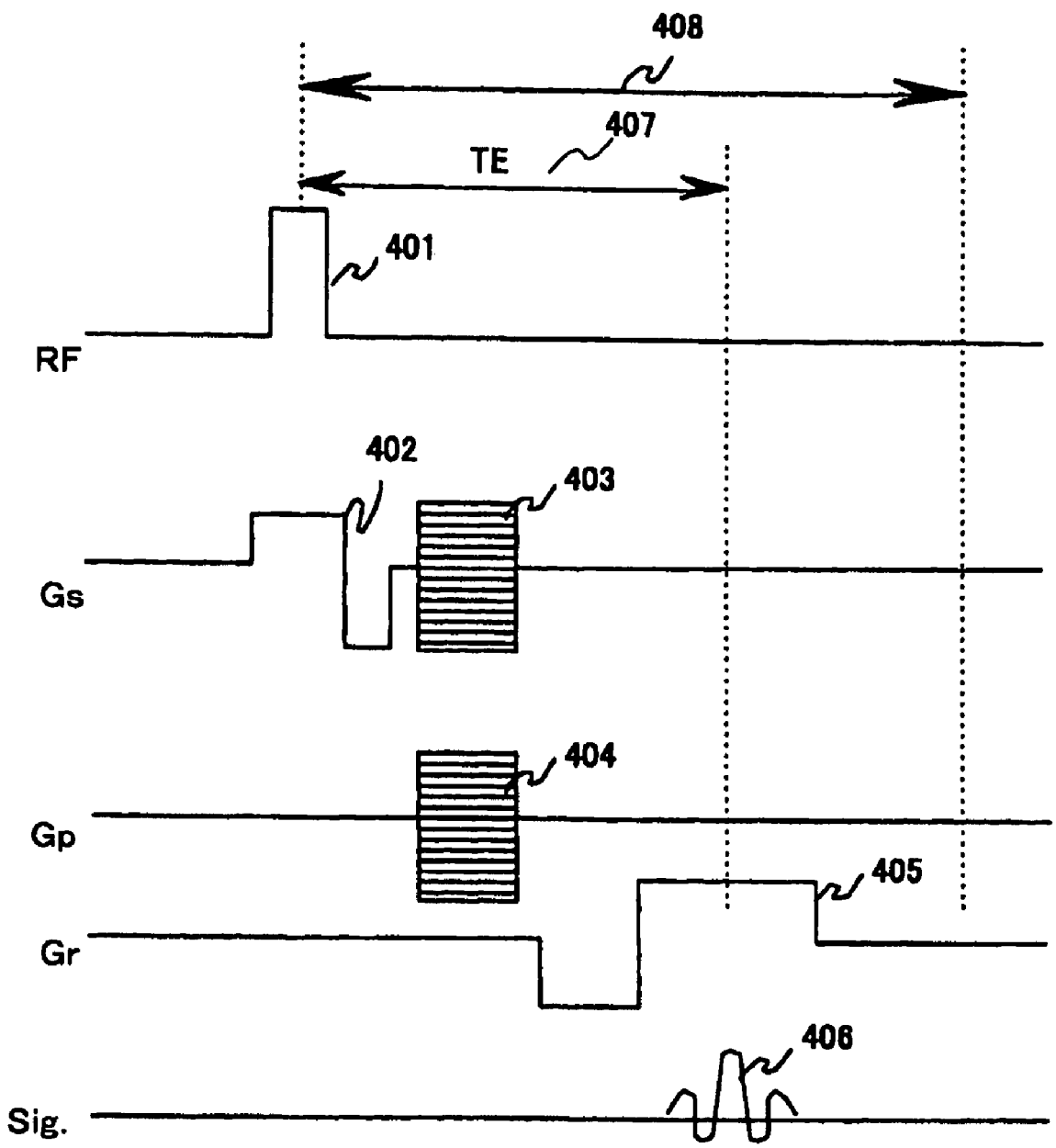
FIG. 4 illustrates an example of an imaging sequence employed by the MRI apparatus of FIG. 1.

FIG. 4 illustrates an example of the imaging sequence that is executed in the MRI apparatus according to the present invention. This imaging sequence is a generic 3D gradient echo sequence, and it firstly applies a high-frequency pulse 401 simultaneously with a slice selective gradient magnetic field 402 so that a predetermined area of the examined subject is excited. A slice (slab) is assumed as a cross section being parallel with the body axis of the examined subject. Thereafter, a slice encoding gradient magnetic field pulse 403 and a phase encoding gradient magnetic field pulse 404 are applied. Next, a readout gradient magnetic field pulse 405 is applied and an echo signal 406 is measured at a point of time after TE time 407 has elapsed since the application of the high-frequency pulse 401. Such measurement as described above is repeated every repetition time 408, while varying intensity of the slice encoding gradient magnetic field pulse 403 and the phase encoding gradient magnetic field pulse 404. Finally, echo signals required for reconstructing one piece of 3D image are measured.

The slice encoding number and the phase encoding number are selected as a combination of values such as 32, 64, 128, 256, and 512, generally for one piece of 3D image. Each echo signal is obtained as a time-series signal made up of sampling data items generally the number of which is 128, 256, 512, or 1024. This data is subjected to 3D Fourier transformation considering a displacement of k-spatial data, whereby 3D image data can be obtained.

Figure 11:
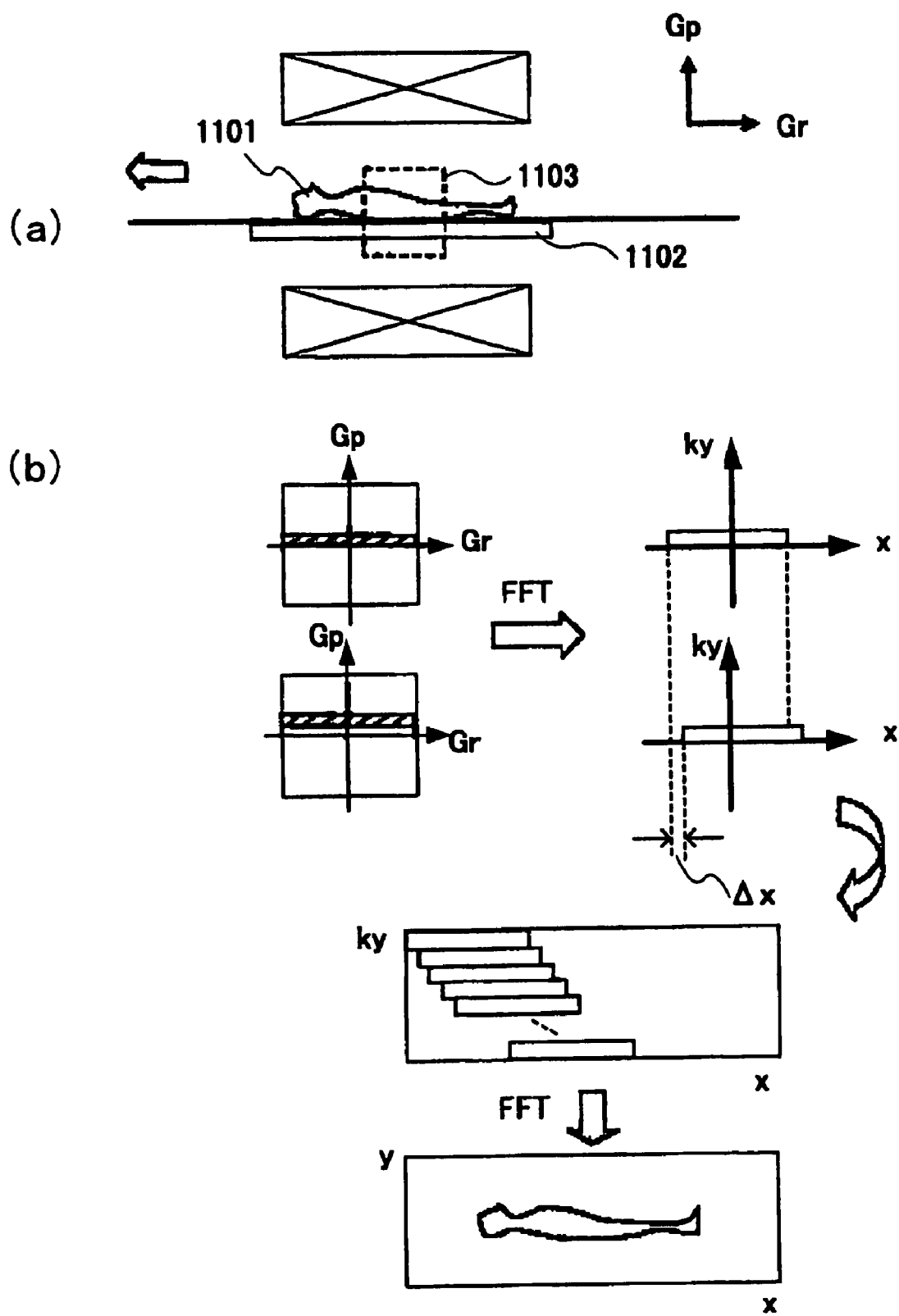
FIG. 11 includes illustrations for explaining the moving bed imaging method.

An image reconstructing method is the same as the image reconstructing method in a publicly known moving bed imaging method. A concept of this method will be explained briefly. As a way of example, as shown in FIG. 11(*a*) and FIG. 12, imaging is continuously performed assuming that a plane parallel to the body axis of the examined subject 1101 is an imaging cross section, and a direction parallel to the moving direction of the bed 102, i.e., the examined subject (the direction indicated by an arrow in the figure) is a readout direction Gr. Here, when the bed 1102 moves in the arrow direction using the point P as a starting point (0), the FOV 1103 is relatively displaced with respect to the examined subject 1101, and the moving velocity of the FOV corresponds to the moving velocity of the bed. When the echo signals obtained by the imaging as described above are subjected to the Fourier transformation in the readout direction, the data (ky-x space data) is displaced in the readout direction (x direction) as shown in FIG. 11(*b*), and finally, it becomes data that fills the ky-x space. Therefore, by subjecting the data filling the ky-x space to the Fourier transformation, an image covering the total length in the x direction can be obtained.

In the moving bed imaging method, COR (coronal) section and/or TRS (transverse) section are typically used, and a moving direction of the bed is a slice direction for the TRS section, and it is a readout gradient magnetic field direction for the COR section. In the present invention, any methods may be applicable, and further it is not limited to these publicly known methods.

In FIG. 4, a sequence of gradient echo system is shown, but other imaging sequence may be employed. As a way of example, DWI (Diffusion Weighted Imaging) sequence based on EPI (Echo Planar Imaging) may be employed, which is a diffusion weighted imaging, or FSE (Fast Spin Echo) may be employed for coronary imaging and a general T2 weighted image. In addition, not only 3D sequence but also 2D sequence or multi-slice sequence is applicable. Further, radial scanning is also applicable.

Next, an operation of the MRI apparatus having the above configuration will be explained.

Figure 12:
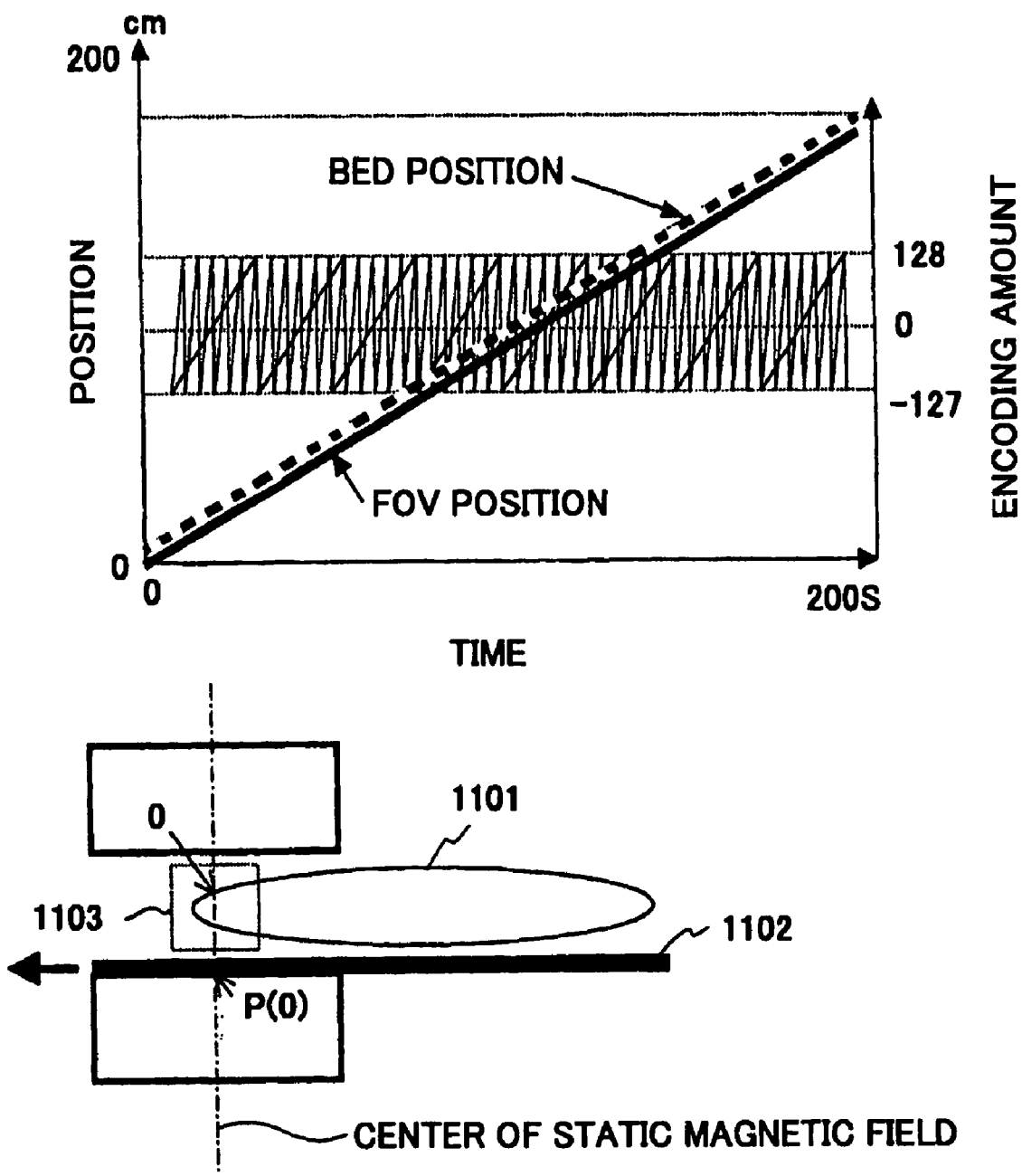
FIG. 12 includes illustrations showing a positional relationship between the FOV and the bed in asynchronous imaging.

The MRI apparatus according to the present embodiment features a synchronous imaging control. However, firstly, an operation in the case of asynchronous imaging will be explained. Control of the asynchronous imaging is similar to the conventional moving bed imaging method, and a time required for imaging a wide imaging region along the moving direction of the bed is calculated to determine a moving velocity Vb of the bed based on this imaging time. In other words, the moving velocity Vb of the bed is configured to be a velocity obtained by dividing the total length of the imaging region by the imaging time. When an imaging sequence is decided, the imaging time is automatically decided according to the TR (repetition time), the encoding number, and the number of FOV of the imaging sequence. While imaging is performed, if the same imaging sequence is executed continuously, the bed moving velocity Vb corresponds to the moving velocity Vf of the FOV position on the examined subject, and it is as shown in FIG. 12. In the graph shown in the upper part of the FIG. 12, the horizontal axis represents a time and the vertical axis represents a position. Two lines respectively represent a change of the bed position and a change of the FOV position during the imaging time. In addition, zigzag lines in the center schematically illustrate a status of imaging during the imaging time, indicating a change of encoding amount. If the imaging pulse sequence is assumed as 2D sequence, the fine zigzag line indicates every one encoding step, and the zigzag line with a large spacing indicates a change of the encoding amount every imaging of one FOV in the phase encoding direction. In addition, if the imaging pulse sequence is assumed as 3D sequence, the fine zigzag line indicates every one slice-encoding step, and the zigzag line with a large spacing indicates a change of the encoding amount every imaging of one FOV in the slice encoding direction. In the lower part of FIG. 12, a relationship between the FOV 1103 and the examined subject 1101 is indicated. In this asynchronous imaging, a position of the FOV 1103 with respect to the center of the static magnetic field may not change.

Figure 5:
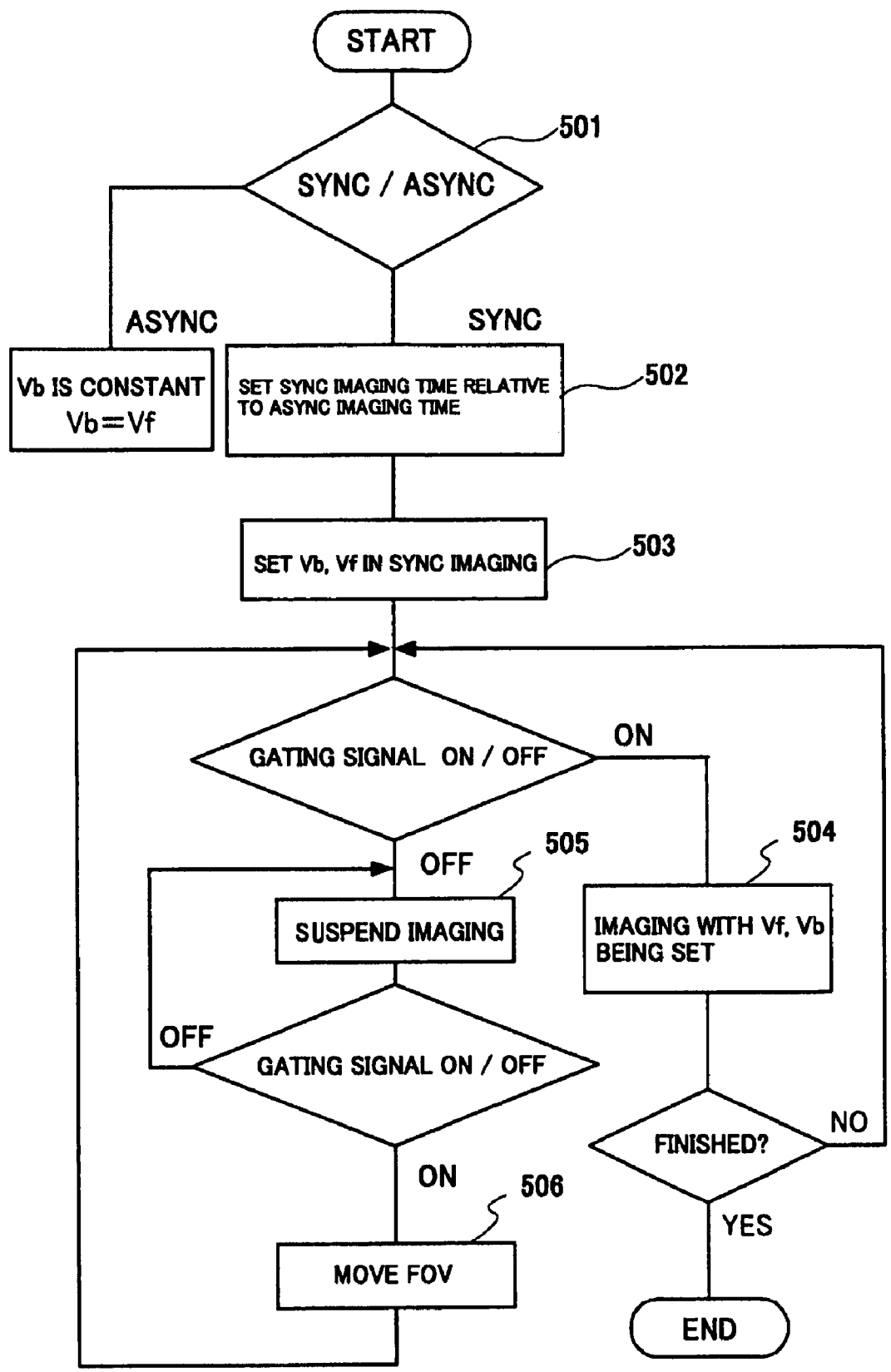
FIG. 5 is a flow diagram that shows an example of operations of moving bed imaging according to a first exemplary embodiment.

Next, an operation of synchronous imaging will be explained. FIG. 5 illustrates a flow of control performed in the synchronous imaging.

Initially, when the synchronous imaging is selected (step 501), as to a targeted imaging portion, a ratio of the imaging velocity of the synchronous imaging is set, relative to the imaging velocity in the case where the synchronous imaging is not performed (in the case of asynchronous imaging) (step 502). When the imaging sequence is decided, the imaging time of the asynchronous imaging is automatically decided according to the TR, the encoding number, and the number of FOV. Therefore, relative to this imaging time for the asynchronous imaging, it is determined how much longer the synchronous imaging time is needed to be, that is, to what extent the imaging velocity is reduced. Such velocity ratio R as described above may be automatically calculated by receiving biological gating signals for a predetermined period of time prior to starting the imaging, and using ON/OFF signals therefrom. Alternatively, a user may manually enter an average value of imaging time of the synchronous imaging for the targeted imaging portion, or an empirical value of the ratio between the synchronous imaging and the asynchronous imaging. For example, in the imaging by the pulse gating, if the imaging is performed at a velocity reduced by 25%, ¼ (=25%) is set. In the case of the heart coronary imaging, 60/200 may be set, if the imaging time T0 in the asynchronous imaging is 60 seconds and the imaging time Tg is 200 seconds in the double gating, i.e., cardiac gating and respiratory gating.

After the ratio R is set in such a manner as described above, based on this ratio R, the bed moving velocity Vb and the moving velocity Vf of the imaging area (FOV) in a coordinate system of the examined subject are determined (step 503). In the normal (asynchronous) moving bed imaging method, a relationship between the bed moving velocity Vb and the moving velocity Vf of the imaging area is established as Vb=Vf. An echo signal is displaced in the readout direction during the repetition time TR of the imaging sequence, and if the displaced amount is assumed as "Δx", the following equation is established: Vb=Vf=Δx÷TR.

On the other hand, in the case of the synchronous imaging, if the bed moving velocity in the asynchronous imaging is assumed as V0, the settings are configured with an aim that the bed moving velocity is defined as: Vb=V0×R (for example, R=T0/Tg). In other words, in the aforementioned example in which the imaging time T0 of the asynchronous imaging is 60 seconds and the imaging time Tg of the synchronous imaging is 200 seconds, if the bed moving velocity at the time of asynchronous imaging is 1 cm per second, imaging is performed by reducing the bed moving velocity to 0.3(≈1 cm/s×60/200) during the synchronous imaging.

In addition, since the moving velocity of the FOV Vf (=Δx÷TR) has to be identical to the imaging velocity, it is assumed that Vf=V0. Accordingly, moving of the imaging area precedes moving of the bed, and the center of the imaging area is displaced from the center of the static magnetic field. In order to resolve this displacement, the imaging is performed while moving the FOV in the apparatus coordinate system in the direction opposite to the bed moving direction (step 504) at a velocity corresponding to a difference from the moving velocity of the bed. Moving of the FOV can be achieved, for instance, by shifting an irradiation frequency as mentioned below. As thus described, while the imaging is performed, a position of the FOV varies momentarily in both the apparatus coordinate system and the examined subject coordinate system.

During the time when the gating signal is OFF in the biological gating method, the imaging is suspended (step 505). The bed is kept moving even while the imaging is suspended. Therefore, when the gating signal is turned ON next, the FOV in the apparatus coordinate system is controlled such that the position in the subject coordinate system should become identical to the FOV position when the imaging was suspended, and obtaining of an echo signal is started (step 506). The controlling of the FOV as described above can be implemented by controlling the FOV position in the apparatus coordinate system, similar to the aforementioned movement of the FOV while the imaging is performed. For example, as for the slice direction, the slice gradient magnetic field and the excited RF pulse frequency are controlled, thereby controlling the FOV position in the apparatus coordinate system. Accordingly, in the subject coordinate system, the imaging can be performed on sequential positions, irrespective of ON/OFF status of the imaging.

Hereinafter, controlling of the irradiation frequency will be explained to move the FOV position.

By using Vb, Vf, and V0 described above, a difference between the moving velocity of the FOV position and the bed moving velocity is calculated. When the difference of the moving velocity is assumed as $V_{shift}$, it is expressed by the following equation:

$$V_{shift}=Vf-Vb=V0(1-R).$$

Now, it is assumed that the imaging start time t=0, the imaging is continuously performed until t=t1, the imaging is suspended from t=t1 to t=t2 until a gating signal (a synchronous signal) occurs, and at the time t=t2, the gating signal is caught, and the imaging is restarted. On this occasion, the displaced amount of the FOV position from the initial imaging stage is calculated utilizing the apparatus coordinate system. If the displaced amount is assumed as ΔX(t), and 0<t<t1, the following equation is established.

$$\Delta X(t)=t \cdot V_{shift}=t \cdot V0(1-R)$$

Under the condition of t1<t<t2, the imaging is not performed, and the FOV position, that is, ΔX(t) is not defined. Under the condition of t1<t<t2, the following equation is established:

$$\begin{aligned}\Delta X(t) &= t1 \cdot V_{shift} - Vb(t2-t1) + (t-t2)V_{shift} \\ &= t1 \cdot V0(1-R) - V0R(t2-t1) + (t-t2)V0(1-R) \\ &= (t1+t-t2)V0(1-R) - V0R(t2-t1)\end{aligned}$$

For the slice gradient magnetic field intensity Gs, a desired irradiation frequency f varies in accordance with the imaging FOV position that varies momentarily. If the variation is assumed as Δf(t), Δf(t)=γGs·ΔX(t)

(In the above equation, "γ" indicates gyromagnetic ratio).

Then, under the condition that 0<t<t1, Δf(t)=γGs{t·V0(1−R)}

Under the condition that t1<t<t2, Δf(t)=γGs{(t1+t−t2)V0(1−R)−V0R(t2−t1)}.

If the bed moved distance while the gating signal is OFF (t1<t<t2) is assumed as Δxb, a desired irradiation frequency f for the slice gradient magnetic field intensity Gs is displaced by Δf with respect to the frequency just before the gating signal is turned OFF, Δf being given by the following equation:

$$\Delta f=\gamma Gs \cdot \Delta xb$$

Figure 6:
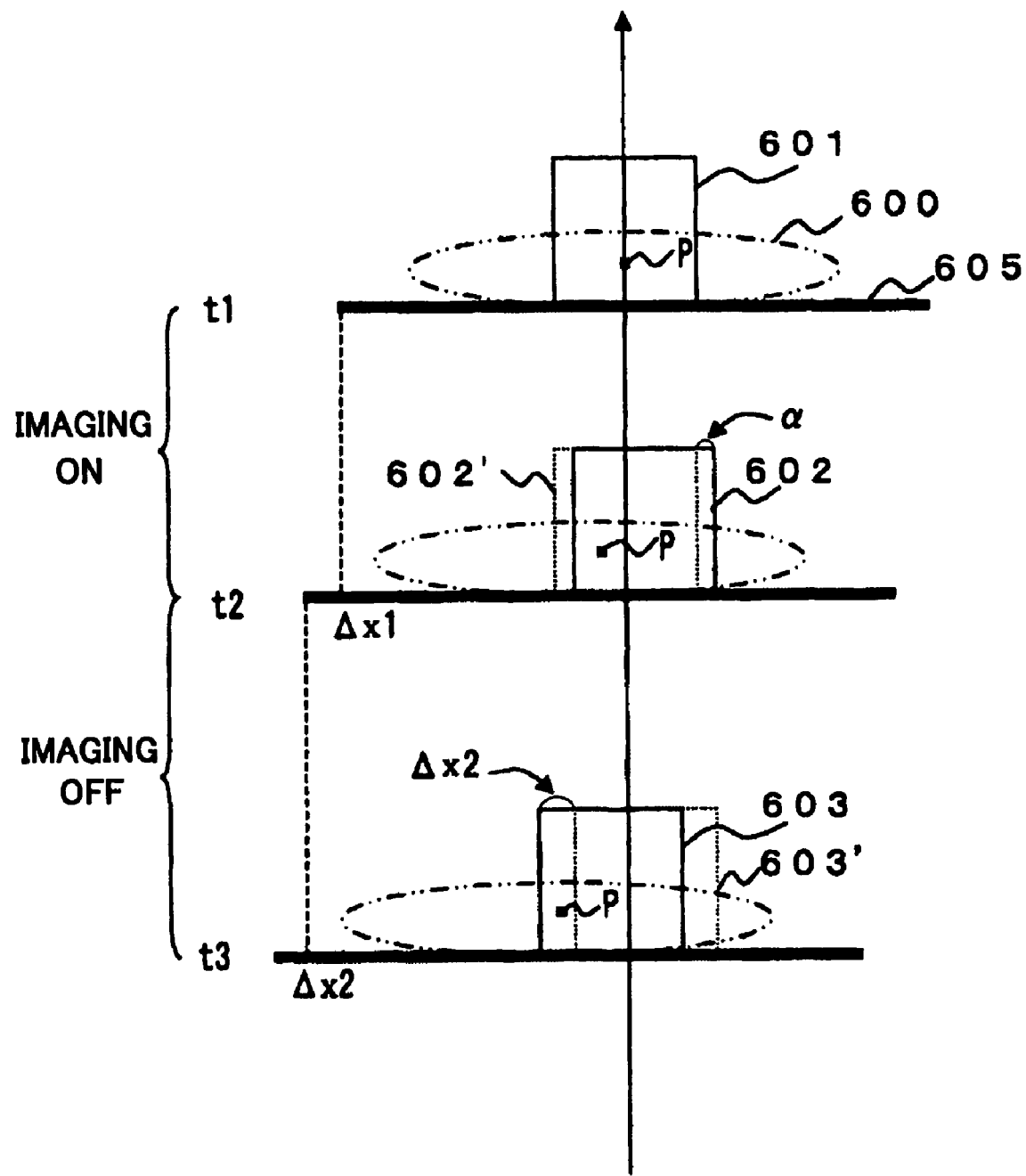
FIG. 6 illustrates a positional relationship among FOV, the bed, and the examined subject.

FIG. 6 illustrates a positional relationship among the FOV, the bed, and the examined subject in the imaging as described above. In the figure, the arrow in the vertical direction indicates a static magnetic field direction passing through the center of the static magnetic field, and it is assumed that the bed 605 moves in a direction orthogonal to the static magnetic field direction. It is further assumed that at the point of time t1 as a start of imaging, the center of the FOV 601 corresponds to the center of the static magnetic field, and it also corresponds to a given point P of the examined subject 600. At the point of time t2 after the imaging proceeds, the bed 605 moves at a moving velocity Vb, and its moved distance becomes Δx1. If the moving velocity Vb of the bed 605 is equal to the moving velocity V of the FOV, a position of the FOV with respect to the center of the static magnetic field is not changed. Therefore, at the point of time t2, the FOV reaches the position 602' indicated by a dotted line. However, since Vf>Vb is defined in the present embodiment, the FOV moves to the position 602 indicated by a solid line. In other words, the position is off the center by α, which is decided by a difference between Vb and Vf. Next, even if the imaging is turned OFF at the point t2 and it is restarted at the point t3, the bed 605 keeps moving at a constant velocity even during this OFF period. Therefore, at the point of time t3 restarting the imaging, the examined subject 600 is also shifted. Here, if the imaging is restarted at the FOV 603' that is identical to the FOV 602 at the point of t2, there is a loss of data corresponding to the bed moved distance Δx2. Accordingly, it is controlled so that the position of FOV in the apparatus coordinate system is shifted to the position 603, and the FOV on the examined subject 600 becomes the same as the FOV at the point of t2. In other words, the position of P in the FOV 602 corresponds to the position P in the FOV 603.

Figure 7:
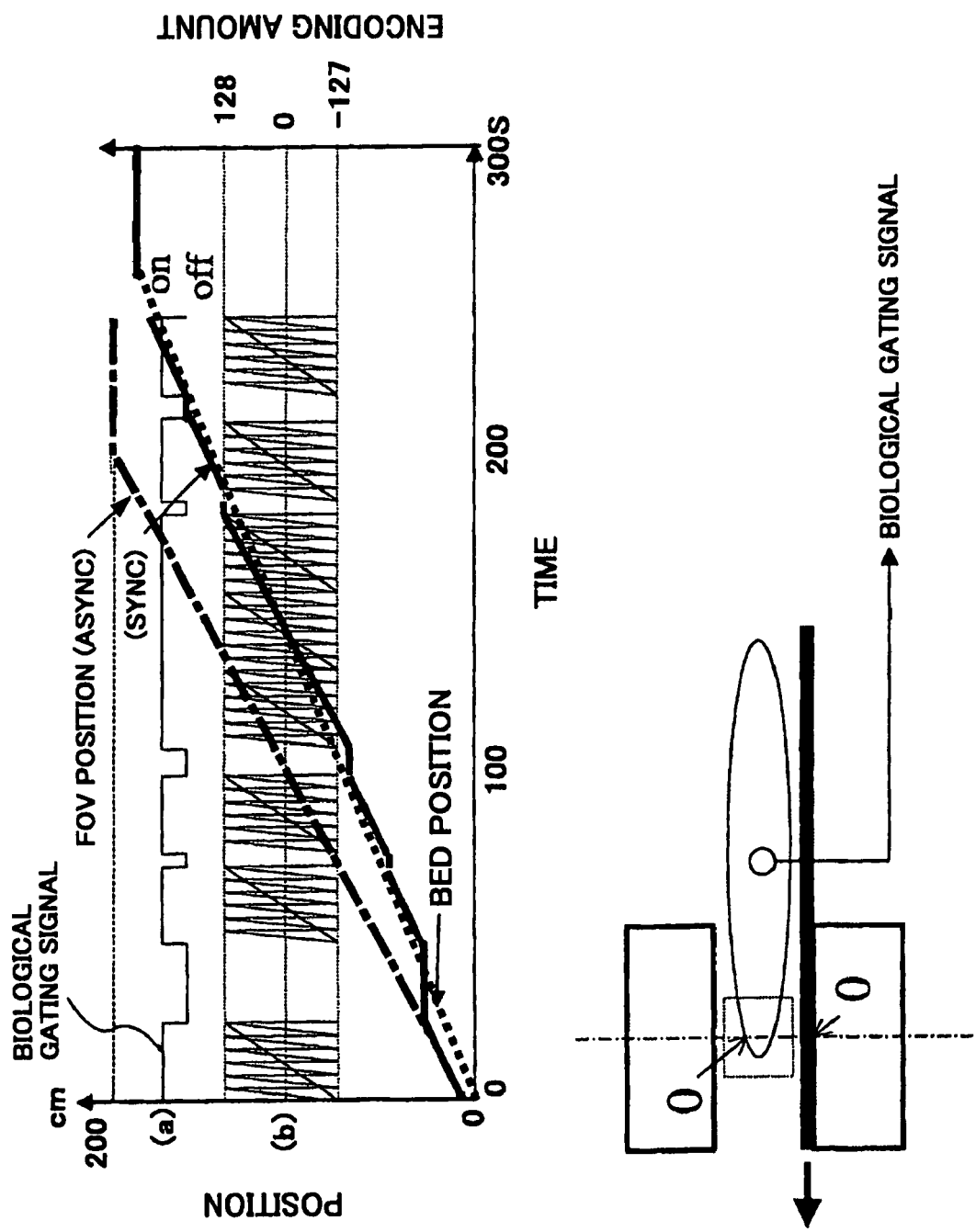
FIG. 7 illustrates a positional relationship between the FOV and the bed according to a first exemplary embodiment.

A relationship between the FOV position (a position in the examined subject coordinate system) and the bed position in the total imaging process is shown in FIG. 7. In the figure, the vertical axis indicates a position of the bed in the bed moving direction, and the horizontal axis indicates a time. The dotted line represents the position of the bed, the solid line represents the FOV position in the synchronous imaging, and the alternate long and short dash line represents the FOV position in the asynchronous imaging. The alternate long and short dash line and an inclined part of the solid line are parallel to each other, representing, respectively, the FOV position in the synchronous imaging and the FOV position in the asynchronous imaging. In other words, the imaging velocity is identical in the both cases. Reference mark (a) schematically indicates a biological gating signal and reference mark (b) schematically indicates variation of the encoding amount in accordance with the imaging. For instance, in the case of 2D sequence, a fine zigzag line indicates each one encoding step, and a zigzag line having a large spacing indicates a change of the encoding amount in the phase encoding direction every imaging of one FOV. Here, the encoding amount represents only the encoding amount in the phase encoding direction. However, in the case of 3D imaging as shown in FIG. 4, the fine zigzag line indicates each one slice-encoding step, and the zigzag line having a large spacing indicates a change of the encoding amount in the slice encoding direction every imaging of one FOV.

As illustrated, since the bed moving velocity is constant, the position of the bed is linearly changed. However, the moving velocity of the FOV position in the imaging time is higher than the bed moving velocity. Therefore, at the time when the gating signal is turned OFF, a moved distance of the bed position is less than the FOV moved distance ($\Delta x$) during the imaging, but the bed keeps moving continuously even while the imaging is OFF by the gating signal. In the meantime, the FOV position in the subject coordinate system is fixed when the gating signal is turned OFF. Therefore, even though there is a time period when no gating signal is obtained, an echo signal being acquired is equivalent to the signal that is obtained by moving the bed continuously. During this period, a displacement between both signals is reduced, and the imaging proceeds in a condition that the bed position approximately corresponds to the imaging FOV position, irrespective of ON/OFF status of the imaging. A slight displacement between the bed position and the FOV position in the course of imaging corresponds to a slight displacement of the FOV with respect to the center of the static magnetic field, and it is ignorable.

The echo signals obtained by the imaging above are subjected to Fourier transformation in the readout direction to obtain hybrid data (ky-x space data). As shown in FIG. 11(*b*), the hybrid data is further subjected to the Fourier transformation in the phase encoding direction, thereby obtaining an image across a wide total imaging area of the examined subject. Reconstruction of the image may be performed after the imaging is completed. However, it is possible to perform Fourier transformation in the ky direction when the hybrid data becomes available in the ky direction, and images in the course of imaging may be sequentially reconstructed and displayed as appropriate.

In the present embodiment, the moving velocity of the bed corresponds to the effective imaging velocity, and the FOV position is kept almost constant in the apparatus coordinate system, allowing an acquisition of an echo signal that is equivalent to the signal obtained when the bed is continuously moved, even though there is a time period when no signal is obtained by the synchronous measurement. Therefore, it is possible to obtain an image of synchronous imaging that not cause artifact due to intermittent imaging during a continuous movement of the bed.

The imaging method to which the present embodiment is applied, includes for example, a cardiac imaging (short axis view, long axis view, four-chamber view, and coronary view) according to the cardiac triggering, or according to the double gating including both the cardiac triggering and the respiratory triggering, non-breath-holding imaging of liver, pulse triggering such as renal artery, coronary artery, and main artery gating, measuring of cardiac triggering blood flow, and the like.

It is to be noted that in the present embodiment, an explanation has been made as to a case where an external body motion sensor is provided as a respiratory monitor. Alternatively, a sequence for generating and obtaining a navigator echo (navigator sequence) can be executed as a function of the body motion monitor. In the navigation sequence, a noted portion (e.g., diaphragm or the like) is locally excited by using the high-frequency magnetic field and the selection gradient magnetic field, and an echo (navigator echo), to which the phase encoding gradient magnetic field is not added, is obtained from this locally excited area. For example, this kind of navigator sequence is executed under the control of the controller 111 as a predetermined sequence, which is combined with the imaging sequence being selected. By executing the navigator sequence, information indicating a position of the examined subject as shown in FIG. 3(*e*) can be obtained, and a gating signal (f) required for the synchronous imaging can be generated.

As thus described, when the navigator echo is used, the MRI detector 106 and the signal processor 107 can act as the biological monitoring machine 115 shown in FIG. 1. Therefore, a body motion monitor independent as hardware is not necessary. Even when the navigator echo is used instead of the body motion monitor, a double gating using a signal from an electrocardiograph is still available.

An example to perform the synchronous imaging has been explained so far as the first embodiment of the present invention. The present invention features that the moving velocity of the bed and the moving velocity of the FOV on the examined subject are independently controlled. Therefore, the present invention is applicable irrespective of a situation whether the imaging is biological gating or not, and accordingly, this provides a way to various imaging. Hereinafter, another embodiment of the present invention will be explained.

Figure 8:
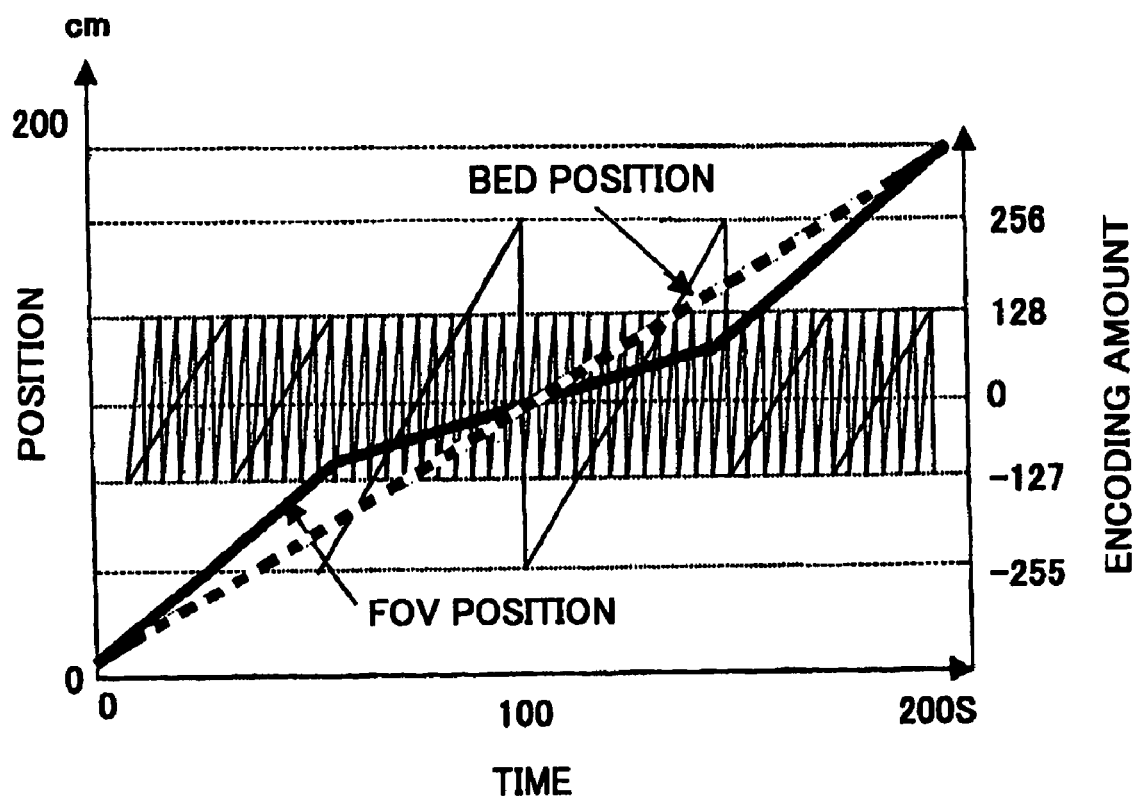
FIG. 8 illustrates positional relationship between the FOV and the bed according to a second exemplary embodiment.

FIG. 8 illustrates the second embodiment. Similar to FIG. 7, the bed position is represented by a dotted line, and the FOV position is represented by a solid line.

Also in the present embodiment, the bed moving velocity is kept constant and the moving velocity is determined considering the total effective imaging time. These settings are the same as the first embodiment. However, in the present embodiment, the imaging itself is performed continuously, and the moving velocity of the FOV in the examined subject coordinate system is made different by area. Specifically, the moving velocity of the FOV in the examined subject coordinate system is set higher than the bed moving velocity in general, but as for a particular portion, the bed moving velocity is made lower so as to obtain an image of high spatial resolution.

In other words, as illustrated, the phase encoding is scanned from −127 to 128 for example in a normal imaging, and obtains data corresponding to one piece of image (in the following, imaging that measures signals of the entire phase encoding amount for one FOV is referred to as "onetime measurement"). On this occasion, the moving velocity of the FOV is higher than the bed moving velocity. However, as for the part to obtain an image of high spatial resolution (the third and fourth measurements in the figure), the phase encoding is scanned, for example, from −255 to 256 to obtain data corresponding to one piece of image. Here, in accordance with the increase of the number of phase encoding, the moving velocity of the FOV is reduced (it becomes ½ in the example shown in the figure), and then, becomes lower than the bed moving velocity. A moved distance of the FOV in the apparatus coordinate system for onetime measurement is the same both at the time of imaging of high spatial resolution and at all other times.

If the FOV moving velocity Vf1 upon normal imaging is assumed as Vf1, and the moving velocity of the imaging of high spatial resolution is assumed as Vf2, the bed moving velocity Vb is expressed by the following equations (1) and (2):

$$Vb = [\text{Bed moved distance}] \div (rT1 + (1-r)T2) \quad (1)$$

$$[\text{Bed moved distance}] = Vf1 \cdot T1 + Vf2 \times T2 \quad (2)$$

Here, "T1" represents [Measuring count of high spatial resolution imaging]×[Onetime measuring time (TR×phase encoding number)] and "T2" represents [Measuring count of normal imaging]×[Onetime measuring time (TR×phase encoding number)]. Here, "r" represents a ratio of [Measuring count of high spatial resolution imaging] to the total measuring count.

Accordingly, if the imaging sequence, together with the imaging sequence of the high spatial resolution imaging, the imaging sequence of the normal imaging, and the measuring count are determined, Vb is automatically obtained from the equations (1) and (2). On the other hand, a user may set the bed moving velocity and the FOV position prior to the imaging, and according to those settings, the controller 111 configures a condition for the high spatial resolution imaging (phase encoding amount).

Figure 13:
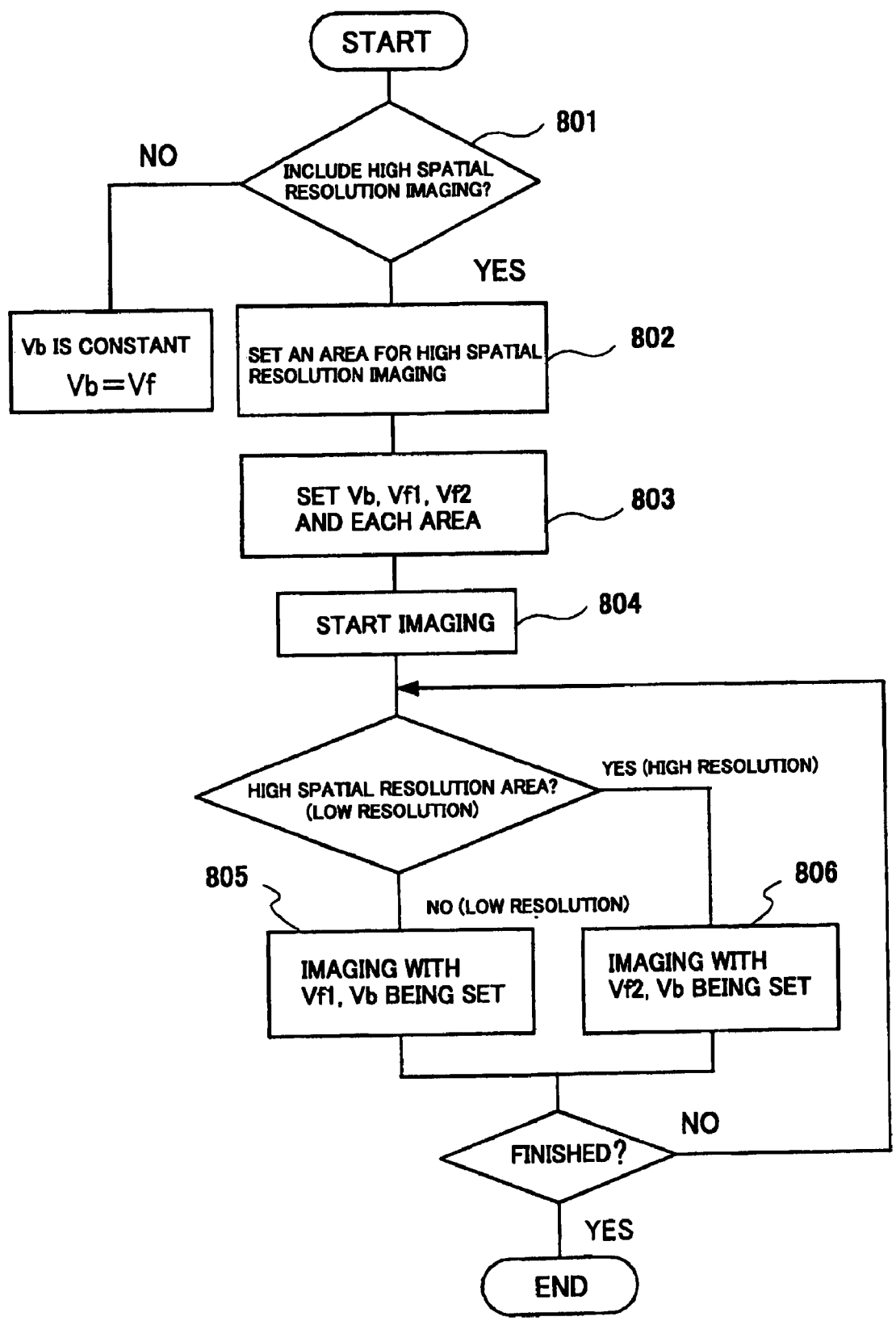
FIG. 13 is a flow diagram showing an example of operations of moving bed imaging according to a second exemplary embodiment.
Figure 14:
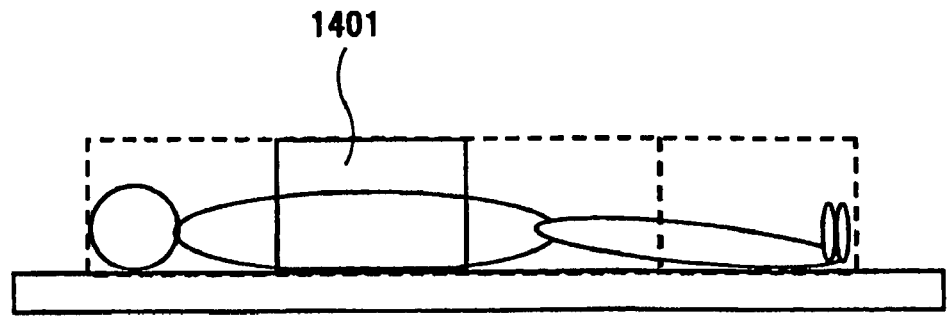
FIG. 14 is an illustration to explain settings of an imaging area and an imaging period in each of the exemplary embodiments of the present invention.

FIG. 13 shows an example of a control flow according to the present embodiment. Firstly, when the imaging is selected including the high spatial resolution imaging (step 801), a designation of area is accepted where the high spatial resolution imaging is performed within the total imaging area (step 802). As shown in FIG. 14, for example, an area on the subject to be examined is designated by displaying on the display unit 108 a total body outline image (scanogram) 1400 of the examined subject, the image having been acquired previously. Then, on this image, a second area is designated as an area for the high spatial resolution imaging 1401. Alternatively, it is possible to input numeric values, for example, a distance or a range from the edge of the total imaging area to configure the settings. On this occasion, conditions or the like for the high spatial resolution imaging may also be configured. With the settings as thus configured, the ratio "r" is calculated, which is a ratio of the measuring count of the high spatial resolution imaging to the total measuring count. Then, the bed moving velocity Vb and FOV moving velocities Vf1 and Vf2 of the normal imaging and the high spatial resolution imaging, respectively, are calculated from the equations (1) and (2), and those calculated values are set (step 803). When the imaging is started (step 804), in the normal imaging, the moving velocity of the FOV on the examined subject is set to be higher than the bed moving velocity, and according to a difference in velocity therebetween, imaging is performed by controlling the FOV position in the apparatus (step 805). In the case of the high spatial resolution imaging area, the FOV moving velocity on the examined subject is set to be lower than the bed moving velocity, and according to a difference in velocity therebetween, imaging is performed by controlling the FOV position in the apparatus, in the direction opposite to the direction in the case of the normal imaging (step 806).

Reaching the high spatial resolution imaging area and the low resolution imaging area can be determined automatically by the first and the second positions designated in step 802 and the bed moving velocity. As for the FOV position on the examined subject, it can be known that the FOV has reached the predetermined area, by the bed position and moved distance detected by the encoder provided on the bed (top board), and the FOV moved distance that is obtained from the relationship between a transmission frequency of the high frequency pulse and the slice selection gradient magnetic field ($\Delta f = \gamma Gs \cdot \Delta xb$).

According to the present embodiment as described above, a part of the total image can be optionally subjected to the high spatial resolution in the moving bed imaging method. Though this may extend the imaging time, an effect of heterogeneity in the magnetic field can be suppressed.

It is to be noted that in the explanation above, two kinds of areas are set, the normal imaging area (first area) and the high spatial resolution area (second area), to make the moving velocity of the FOV position different between those areas. However, three or more kinds of areas, such as a low spatial resolution area, a normal imaging area, and a high spatial resolution area may be provided, so as to control the moving velocity of the FOV in each of those areas.

In the embodiment described above, an explanation has been made as to a case where the second area is configured as the high spatial resolution area. However, it is further possible to make the second area as a target of imaging with a body motion monitoring including a collection of navigator echo. If an image of a large area of the examined subject is acquired, the body motion monitor is not needed so much for the head and the legs, but it is effective for imaging an abdominal and chest region (area 1401 in FIG. 14, for example). If the collection of the navigator echo as a function of the body motion monitor is added to the collection of a signal for image reconstruction, the TR (repetition time) is extended and the imaging time is elongated. However, similar to the case of the aforementioned high spatial resolution imaging area, the moving velocity of the FOV on the examined subject is set to be lower than the bed moving velocity for imaging this particular area, and corresponding to a difference in velocity therebetween, the FOV position in the apparatus is controlled to move in a direction opposite to the direction for the case of normal imaging. Accordingly, it is possible to execute the imaging with the body motion monitor only within the second area, without changing the bed moving velocity. In the imaging with the body motion monitor added as described above, the aforementioned synchronous imaging can be combined therewith, that is, a result of the body motion monitor may be used as a gating signal, or the navigator echo may be used for correcting a final position of the image.

It is further possible to perform a high SN (signal to noise ratio) imaging for the second area in the second embodiment. In the second area where the high SN imaging is performed, for example, the number of times for adding signals acquired in an identical phase encoding, is set to be larger than the first area, thereby achieving the high SN. In the case above, in step 802 in FIG. 13 where an area is configured, the area for the high SN imaging and the number of times for adding signals (average number of times) are configured. With the settings above, the ratio "r" of the measuring count of the high SN imaging to the total measuring count is calculated, and according to the equations (1) and (2), the bed moving velocity Vb, the moving velocities Vf1 and Vf2 of the FOV respectively in the normal imaging and in the high SN imaging are calculated and configured.

Accordingly, in the case of the normal imaging, the moving velocity of the FOV on the examined subject is set to be higher than the bed moving velocity, and in the case of the high SN imaging, the FOV moving velocity on the examined subject is set lower than the bed moving speed, whereby the high SN imaging can be performed partially (that is, only the part requiring a detailed observation), without changing the bed moving velocity.

Figure 9:
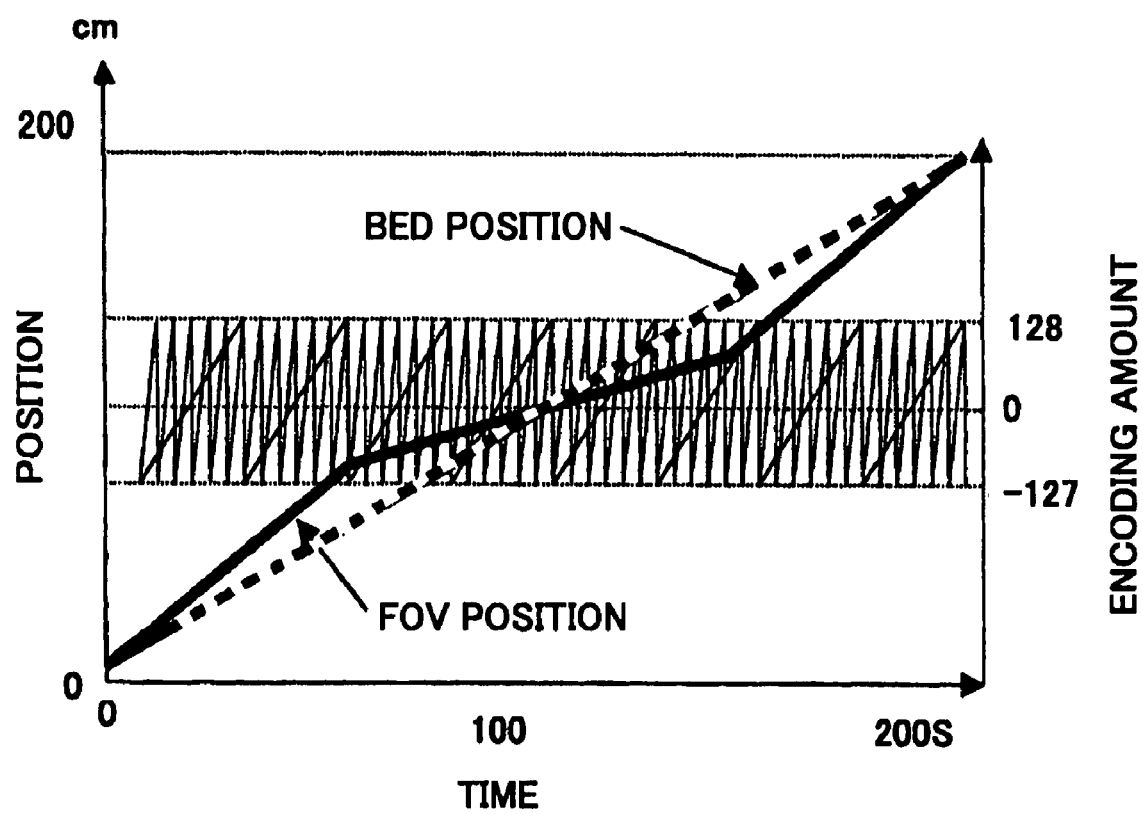
FIG. 9 illustrates a positional relationship between the FOV and the bed according to the third embodiment.

FIG. 9 illustrates the third embodiment. Also in the present embodiment, the bed moving velocity is kept constant while the FOV moving velocity is varied area-by-area, and these settings are the same as the second embodiment. However, in the present embodiment, the phase encoding number is kept constant all over the imaging, for example, scanning from −127 to 128 to obtain one image, and the moving velocity of the FOV in the apparatus coordinate system is controlled to be changed area-by-area. In other words, as a way of example, in the first and the second measurements, the FOV position is moved at a velocity higher than the bed moving velocity. However, in the third and the fourth measurements, the moved distance of the imaging area in the apparatus coordinate system is set to be half of distance in the first and the second measurements, and the velocity of the FOV position in the subject coordinate system is reduced to half. Here, controlling of the imaging area movement in the apparatus coordinate system is implemented by controlling, for example, a gradient magnetic field in the slice direction and the frequency of RF pulse, as explained in the description of the first embodiment.

In order to execute the control according to the present embodiment, for example, an area is configured where the FOV position is moved at a velocity lower than a normal status, and according to a range of the area and a ratio how much the velocity is reduced, an imaging time for the whole area is calculated, thereby setting the bed moving velocity. Similar to the second embodiment, the area is configured by designating the area and/or inputting a numeric value, using the scanogram displayed on the display unit. In performing the imaging, firstly, it is performed at a normal moving velocity of the FOV position, that is, at an FOV position moving velocity that is higher than the bed moving velocity. When the bed has moved and the imaging area has reached an area being configured, the FOV position moving velocity is reduced to a low velocity being configured and the imaging is performed. During this time, the bed moving velocity and the imaging velocity are not changed. However, according to a difference between the FOV position moving velocity on the examined subject and the bed moving velocity, the FOV in the apparatus coordinate system is changed.

In the present embodiment, the moving velocity of the FOV is reduced as to a part of area, and therefore it is suitable for the imaging in which timing is crucial, for example, imaging the kidney and/or the liver in timely manner, while observing a substance of the kidney and/or liver being dyed by an injected contrast agent.

When the present embodiment is applied to the imaging with a contrast agent, the bed moving velocity is set to be identical to an average velocity of the moving velocity of the contrast agent in the bed moving direction (simply referred to as "contrast agent moving velocity"), for example, and the moving velocity of the FOV on the examined subject is controlled according to a difference from the bed moving velocity and the contrast agent moving velocity in the imaging area. When the bed moving velocity is higher than the FOV moving velocity, the FOV position is moved to a direction opposite to the bed moving direction. When the bed moving velocity is lower than the FOV moving velocity, the FOV position is moved to a direction being the same as the bed moving direction. Accordingly, the moving velocity of the FOV on the examined subject is made almost the same as the contrast agent moving velocity, whereby it is possible to perform imaging following the contrast agent moving velocity.

Figure 10:
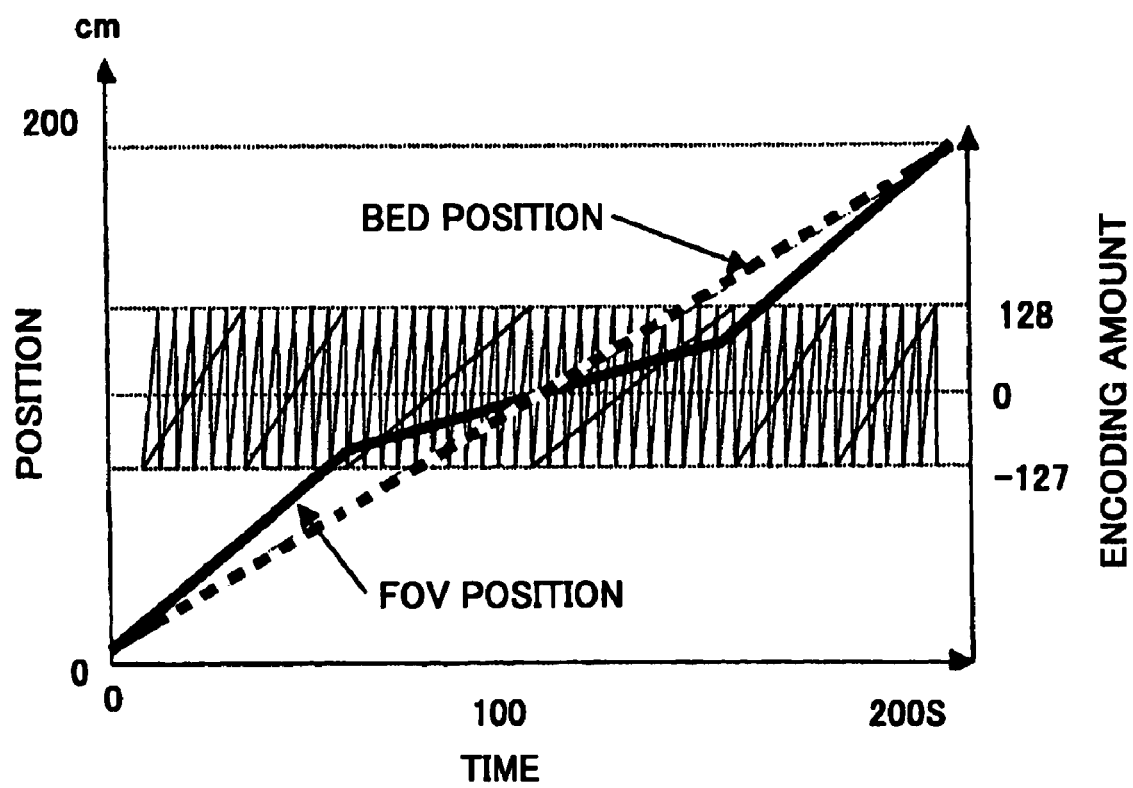
FIG. 10 illustrates a positional relationship between the FOV and the bed according to a fourth exemplary embodiment.

FIG. 10 illustrates the fourth embodiment. Also in the present embodiment, a test object area in which the FOV moving velocity is made different is configured in advance, prior to imaging, and the bed moving velocity is kept constant while the FOV moving velocity is varied area-by-area. These settings are the same as the second and the third embodiments. In the present embodiment, the phase encoding number is kept constant for the entire imaging, and the slice number during one measurement is increased, thereby reducing the moving velocity of the FOV position.

Specifically, for example, in the first and the second measurements, the FOV position is moved at a velocity higher than the bed moving velocity, and one slice image is obtained by onetime measurement. In the third and the fourth measurements, the slice number becomes two within the same TR. Therefore, as illustrated, the slope of the line segment representing the phase encoding (scanning −127 to 128) becomes half of the slope in the case of the first and the second measurements. A moved distance of the imaging area in the apparatus coordinate system within one measurement is common in all the measurements.

Also in the present embodiment, the imaging time is extended due to the increase of the slice number. However, by making the bed moving velocity different from the moving velocity of the FOV position, and by appropriately controlling the FOV position in the apparatus coordinate system, it is possible to suppress the effect of heterogeneity in the static magnetic field to the minimum irrespective of the extension of the imaging time.

The second, the third, and the fourth embodiments have been explained so far, and those embodiments limit neither the way how to reduce the velocity nor the slice number being explained. Time allowance generated by making the bed moving velocity different from the FOV moving velocity is available for various kinds of practical use. As a way of example, TR may be extended to be applied to the extended imaging time. For this case, the present invention is applicable in the similar manner as the fourth embodiment, except that the width of one encoding step (a spacing of fine zigzag line) is enlarged in the third and the second measurements shown in FIG. 10.

Figure 15:
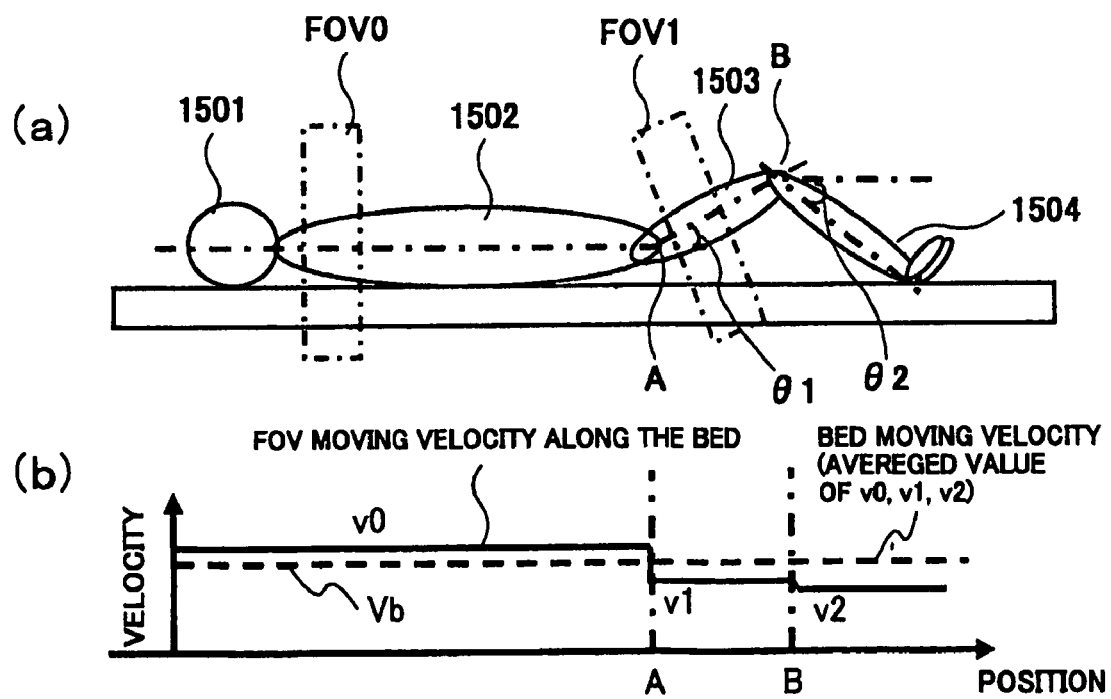
FIG. 15 includes illustrations to explain a fifth exemplary embodiment of this disclosure.

Next, the fifth embodiment of the present invention will be explained. As shown in FIG. 15(a), the present embodiment is applied to the case where a part of the examined subject is inclined with respect to the moving direction of the bed.

In the present embodiment, as shown in the example of FIG. 15(a), the head part 1501 and the body trunk 1502 are subjected to imaging on a cross section (FOV0), which is vertical to the bed. When the imaging has reached the femoral region 1503 (point A in the figure), the imaging section is set as the imaging section (FOV1) that is inclined only by angle θ1, following the bending of the femoral region. When the imaging has reached the knee joint 1504 (point B in the figure) the imaging section is set as the imaging section (FOV2) that is inclined only by the angle θ2, following the bending of the distal lower extremity. Here, in order that the bed moving velocity is made constant and the moving velocity in the cross-section direction of each of the imaging sections (FOV1 and FOV2) is to be the same as the bed moving velocity, it is desirable that the moving velocities v1 and v2 of FOV1 and FOV2 along the bed (a velocity opposite to the bed moving direction) are defined as the following, assuming the bed moving velocity being v0:

$$V1 = v0 \cdot \cos \theta 1$$

$$V2 = v0 \cdot \cos \theta 2$$

Specifically, the bed moving velocity Vb is set to be an averaged value of v0, v1, and v2, and according to a difference between this bed moving velocity Vb being set and each of the imaging section moving velocities v0, v1, and v2, the imaging is continuously performed while the imaging section is finely adjusted ((b) in the figure). In this way, the present invention can be applied also in the case where the moving velocity of the imaging section (FOV) in the bed moving direction is varied depending on the oblique of the imaging section.

It is further possible to combine any of the second to the fifth embodiments appropriately according to the imaging area. In the second to the fifth embodiments, an explanation has been made, combining a situation where the FOV moving velocity is higher than the bed moving velocity and a situation where the FOV moving velocity is lower than the bed moving velocity. However, only either one of the situations (for example, Vb<Vf) can be implemented. In other words, in the embodiment described above, only the case where the bed moved distance finally coincides with the moved distance of the FOV on the examined subject has been explained. Even if the FOV is displaced from the static field center, caused by a difference in velocity between Vb and Vf, such displacement is acceptable as far as an effect exerted by the displacement onto an image is ignorable.

The present invention is the most effective in the case where the bed moving velocity is kept constant, and the FOV moved distance varies depending on whether the imaging is ON or OFF, and/or depending on a targeted imaging area. However, it is not limited to the situation where the bed moving velocity is constant. As a way of example, the present invention is applicable to a case where the entire imaging area is subjected to imaging at two separate times, that is, the bed is suspended in the course of imaging, or there is a period when the bed moving velocity varies in the course of imaging. In the case above, controlling of the bed movement independently of the aforementioned FOV movement may produce an advantage. If the bed moving velocity varies, being switched at multiple stages, the present invention is applicable at the velocity on each stage. Alternatively, the FOV may be moved, while the bed moving velocity is varied continuously.

If the imaging according to the present invention is executed, the size of FOV may be kept constant while the entire imaging is performed, or the FOV may be moved while changing the FOV size. As a way of example, the FOV size is configured to be large in the body trunk with gaining the moving velocity of the FOV for the examined subject, and the FOV size is configured to be small in the lower extremity with reducing the moving velocity of the FOV for the examined subject.

Furthermore, the MRI apparatus according to the present invention may display graphs (FIG. 7 to FIG. 10) on an I/O unit (user interface), the graphs showing the bed position and the FOV position plotted on the time axis. Accordingly, the user is allowed to input and check a necessary imaging condition, thereby enhancing operability in executing the present invention.

INDUSTRIAL APPLICABILITY

According to the present invention, when a bed is continuously moved and an area wider than an FOV of an apparatus is subjected to imaging, a moving velocity of the FOV on a test object is controlled independently of the bed moving velocity, whereby a load onto the examined subject caused by fluctuations of the bed moving velocity is reduced, and it is possible to perform imaging responding to various imaging conditions and requests, which are different by portion in this wide area.

What is claimed is:

1. A nuclear magnetic resonance imaging method that acquires an image of an imaging region of a subject to be examined, in a static magnetic field space of a nuclear magnetic resonance imaging apparatus provided with an FOV being desirable, the imaging region being wider than the FOV, while moving a transport unit having the examined subject thereon, comprising,
    a step that moves the examined subject so that the imaging region of the examined subject passes through the space for imaging,
    a step that relatively displaces the FOV with respect to the examined subject, in response to information obtained from the examined subject during at least a part of a period when the examined subject is being moved,
    a step that executes an imaging pulse sequence while the examined subject is being moved, and collects nuclear magnetic resonance signals from the examined subject, and
    a step that reconstructs an image of the wide imaging region of the examined subject, by using the nuclear magnetic resonance signals.

2. The nuclear magnetic resonance imaging method according claim 1, wherein,
    in the step that relatively displaces the FOV,
    the information obtained from the examined subject is biological information detected from the examined subject, and
    a moving velocity of the FOV for the examined subject is controlled to be different from each other between in a first period and in a second period while acquiring an image of the imaging region, in response to this biological information.

3. The nuclear magnetic resonance imaging method according to claim 2, wherein,
    in the step that relatively displaces the FOV,
    a direction of the relative displacement is controlled to be different from each other between in the first period and in the second period.

4. The nuclear magnetic resonance imaging method according to claim 1, comprising,
    a step that configures settings for a first area and a second area within the imaging region, prior to the step that collects the nuclear magnetic resonance signals,
    further comprising in the step that relatively displaces the FOV, a step that acquires positional information of the FOV for the examined subject, wherein,
    the information obtained from the examined subject is information indicating reaching that the FOV has reached each of the areas, and
    a moving velocity of the FOV for the examined subject is controlled to be different from each other between in the first area and in the second area, in response to the information indicating the reaching.

5. The nuclear magnetic resonance imaging method according to claim 4, wherein, in the step that relatively displaces the FOV, the direction of the relative displacement is controlled to be different from each other in the first area and in the second area.

6. The nuclear magnetic resonance imaging method according to claim 2, wherein, in the step that collects the nuclear magnetic resonance signal, imaging of at least a part of the imaging region includes a synchronous imaging by using the biological information, the imaging is executed in the first period in response to the biological information, the imaging is suspended in the second period in response to the biological information, the direction of the relative displacement is opposite to the moving direction of the examined subject in the first period, and the direction of the relative displacement is the same as the moving direction of the examined subject in the second period.

7. The nuclear magnetic resonance imaging method according to claim 6, wherein, in the step that collects the nuclear magnetic resonance signal, the biological information is acquired from a biological signal obtained from at least one of the electrocardiograph, the sphygmograph, and body motion monitor, in the step that moves the examined subject, a moving velocity of the transport unit is determined by a total imaging time including the first period and the second period and a distance the transport unit has traveled for acquiring an image of the imaging region, in the step that relatively displaces the FOV, the moving velocity of the FOV for the examined subject within the first period is determined by the total imaging time when no synchronous imaging is performed, and a distance that the transport unit has traveled for acquiring the image of the imaging region, and the imaging is executed from a position of the FOV at the point when the imaging is suspended, and in the second period, the moving velocity of the FOV for the examined subject is set to zero and the position of the FOV for the examined subject is not moved.

8. The nuclear magnetic resonance imaging method according to claim 4, wherein, in the step that collects the nuclear magnetic resonance signals, imaging of the second area includes, collecting of the nuclear magnetic resonance signals required for reconstructing a test object image, and collecting of the nuclear magnetic resonance signal required for detecting a body motion of the examined subject, and in the step that relatively replaces the FOV, the moving velocity of the FOV for the examined subject is controlled to be lower in the second area than in the first area.

9. The nuclear magnetic resonance imaging method according claim 4, wherein, in the step that configures settings of each of the areas, an imaging condition in the first area is set to be different from the imaging condition in the second area, and in the step that relatively displaces the FOV, the moving velocity of the FOV for the examined subject is controlled to be different from each other between in the first area and in the second area, in response to each of the imaging conditions.

10. The nuclear magnetic resonance imaging method according to claim 9, wherein, in the step that configures settings of each of the areas, the imaging conditions are set such that the second area should have a spatial resolution higher than the first area, and in the step that relatively displaces the FOV, the moving velocity of the FOV for the examined subject is controlled to be lower in the second area than in the first area.

11. The nuclear magnetic resonance imaging method according to claim 10, wherein, in the step that configures settings of each of the areas, the imaging condition for the second area is set in such a manner that at least one of a slice number, a phase encoding number, and a slice encoding number is increased relative to the imaging condition for the first area.

12. The nuclear magnetic resonance imaging method according to claim 9, wherein, in the step that configures settings of each of the areas, the imaging conditions are set such that the second area should have a higher SN than the first area, and in the step that relatively displaces the FOV, the moving velocity of the FOV for the examined subject is controlled to be lower in the second area than in the first area.

13. The nuclear magnetic resonance imaging method according to claim 12, wherein, in the step that configures settings of each of the areas, the imaging conditions are set in such a manner that a number of averaging the nuclear magnetic resonance signals is increased in the imaging condition for the second area, relative to the imaging condition for the first area.

14. The nuclear magnetic resonance imaging method according to claim 9, wherein, in the step that configures settings of each of the areas, the imaging conditions are set in such a manner chat a size of the FOV in the first area and a size of the FOV in the second area are different from each other.

15. The nuclear magnetic resonance imaging method according to claim 4, wherein, in the step that collects the nuclear magnetic resonance signals includes an imaging using a contrast agent, in the step that configures settings of each of the areas, the first area and the second area are configured in such a manner that in the second area, the contrast agent moves at a velocity lower than the first area, and in the step that relatively moves the FOV, the moving velocity of the FOV for the examined subject is controlled to be lower in the second area than in the first area.

16. The nuclear magnetic resonance imaging method according to claim 15, further comprising a step that obtains a mean flow velocity of the contrast agent within the imaging region, prior to the step that configures settings of each of the areas, wherein, in the step that moves the examined subject, the moving velocity of the transport unit is assumed as he mean flow velocity, and in the step that relatively displaces the FOV, in order that the moving velocity or the FOV for the examined subject accords with the moving velocity of the contrast agent, a moving direction of the FOV for the examined subject is set to be opposite to the moving direction of the examined subject in the first area, and the moving direction of the FOV for the examined subject is made to be the same as the moving direction of the examined subject in the second area.

17. The nuclear magnetic resonance imaging method according to claim 4, wherein,
in the step that configures settings of each of the areas, the first area and the second area are configured in such a manner that the second area is set in an area where a body axis direction of the examined subject and the moving direction of the examined subject form a larger angle than in the first area, and
in the step that relatively displaces the FOV, the moving velocity of the FOV for the examined subject in the moving direction of the examined subject is controlled to be lower in the second area than in the first area.

18. The nuclear magnetic resonance imaging method according to claim 17, wherein,
in the step that relatively displaces the FOV, the FOV is moved along the body axis direction, and
the moving velocity of the FOV in the body axis direction is made approximately identical between the first area and the second area.

19. The nuclear magnetic resonance imaging method according to claim 1, wherein,
in the step that collects the nuclear magnetic resonance signals from the examined subject, a high-frequency magnetic field is applied for exciting the FOV, and
in the step that relatively moves the FOV, a frequency of the high-frequency magnetic field is controlled so as to control die relative displacement of the FOV.

20. The nuclear magnetic resonance imaging method according to claim 1, wherein
in the step that moves the examined subject, the moving velocity of the examined subject is kept constant during a period for acquiring an image of the imaging region.

21. The nuclear magnetic resonance imaging method according in claim 2, wherein,
in the step that moves the examined subject, the moving velocity of the examining subject is controlled to be different from each other between in the first period and in the second period.

22. The nuclear magnetic resonance imaging method according to claim 1, wherein,
in the step that reconstructs the image, an image of a part of the imaging region is reconstructed based on the nuclear magnetic resonance signals that have been obtained so far within at least a part of the period for acquiring an image of the imaging region.

23. A nuclear magnetic resonance imaging apparatus comprising,
a transport unit that transports a subject to be examined within a static magnetic field space including a desired FOV,
an information obtaining unit that obtains information from the examined subject,
a magnetic field application unit that applies a high-frequency magnetic field and a gradient magnetic field to the examined subject,
a control means that controls the transport unit and the magnetic field application unit, and
a signal processing unit that receives nuclear magnetic resonance signals generated from the examined subject to construct an image, wherein,
in the nuclear magnetic resonance imaging apparatus that acquires the nuclear magnetic resonance signals while the examined subject is moved by the transport unit, and acquires an image of an imaging region wider than the FOV,
the control unit controls the magnetic field application unit in such a manner that the FOV is relatively displaced with respect to the examined subject, in response to the information from the examined subject, during at least a part of a period when the examined subject is moving.

24. The nuclear magnetic resonance imaging apparatus according to claim 23, wherein,
the information obtaining unit that obtains information from the examined subject, obtains biological information from the examined subject, and
the control unit controls the magnetic field application unit, in response to the biological information, in such a manner that the moving velocity of the FOV for the examined subject is made different from each other between in a first period and in a second period, while an image of the imaging region is acquired.

25. The nuclear magnetic resonance imaging apparatus according to claim 23, wherein,
the information obtaining unit that obtains information from the examined subject, further obtains positional information of the FOV for the examined subject, and finds information indicating reaching that the FOV has reached the first area and the second area within the imaging region configured in advance, and
the control unit controls the magnetic field application unit, in response to the information indicating the reaching, in such a manner that the moving velocity of the FOV for the examined subject is made different from each other between in the first period and in the second period.

26. The nuclear magnetic resonance imaging apparatus according to claim 24, wherein,
the information obtaining unit that obtains the biological information is at least one of an electrocardiograph, a sphygmograph, and a body motion monitor, and
the control unit controls the magnetic field application unit in such a manner that the imaging is executed during the first period in response to the biological information, and the imaging is suspended during the second period in response to the biological information.

27. The nuclear magnetic resonance imaging apparatus according to claim 25, wherein,
the information obtaining unit that obtains the positional information of the FOV comprises an encoder provided on the transport unit, and obtains the positional information of the FOV on the examined subject based on information from the encoder and a frequency of the high-frequency magnetic field.

28. A nuclear magnetic resonance imaging method that acquires an image of an imaging region of a subject to be examined, in a static magnetic field space of a nuclear magnetic resonance imaging apparatus provided with an FOV being desirable, the imaging region being wider than the FOV, while moving a transport unit having the examined subject thereon, comprising,
a step that moves the examined subject so that the imaging region of the examined subject passes through the space for imaging,
a step that makes a moving velocity of a FOV position higher than a bed moving velocity, in response to information obtained from the examined subject during at least a part of a period when the examined subject is being moved, a step that executes an imaging pulse sequence while the examined subject is being moved, and collects nuclear magnetic resonance signals from the examined subject, and a step that reconstructs an image of the wide imaging region of the examined subject, by using the nuclear magnetic resonance signals.

29. A nuclear magnetic resonance imaging method that acquires an image of an imaging region of a subject to be examined, in a static magnetic held space of a nuclear magnetic resonance imaging apparatus provided with an FOV being desirable, the imaging region being wider than the FOV, while moving a transport unit having the examined subject thereon, comprising, a step that moves the examined subject so that the imaging region of the examined subject passes through the space for imaging, a step that relatively changes a FOV position on the examined subject, in response to information obtained from the examined subject during at least a part of a period when the examined subject is being moved, a step that executes an imaging pulse sequence while the examined subject is being moved, and collects nuclear magnetic resonance signals from the examined subject, and a step that reconstructs an image of the wide imaging region of the examined subject, by using the nuclear magnetic resonance signals.

* * * * *